US009937335B2

(12) United States Patent
Moss et al.

(10) Patent No.: US 9,937,335 B2
(45) Date of Patent: Apr. 10, 2018

(54) DRUG DELIVERY DEVICE EMPLOYING WICKING RELEASE WINDOW

(75) Inventors: John A. Moss, Sierra Madre, CA (US); Thomas J. Smith, Santa Monica, CA (US); Marc M. Baum, Pasadena, CA (US)

(73) Assignee: OAK CREST INSTITUTE OF SCIENCE, Pasadena, CA (US)

( * ) Notice: Subject to any disclaimer, the term of this patent is extended or adjusted under 35 U.S.C. 154(b) by 644 days.

(21) Appl. No.: 14/124,517

(22) PCT Filed: Jun. 6, 2012

(86) PCT No.: PCT/US2012/041159
§ 371 (c)(1),
(2), (4) Date: Jun. 17, 2014

(87) PCT Pub. No.: WO2012/170578
PCT Pub. Date: Dec. 13, 2012

(65) Prior Publication Data
US 2014/0296834 A1    Oct. 2, 2014

Related U.S. Application Data

(60) Provisional application No. 61/520,152, filed on Jun. 6, 2011.

(51) Int. Cl.
| A61M 31/00 | (2006.01) |
| A61K 9/00 | (2006.01) |
| A61K 47/32 | (2006.01) |
| A61K 47/34 | (2017.01) |
| A61K 47/38 | (2006.01) |

(52) U.S. Cl.
CPC ......... *A61M 31/002* (2013.01); *A61K 9/0036* (2013.01); *A61K 47/32* (2013.01); *A61K 47/34* (2013.01); *A61K 47/38* (2013.01)

(58) Field of Classification Search
CPC ........ A61K 47/32; A61K 47/34; A61K 47/38; A61K 9/0036; A61M 31/002
USPC ................................. 604/285, 515; 424/400
See application file for complete search history.

(56) References Cited

U.S. PATENT DOCUMENTS

| 3,630,200 A | 12/1971 | Higuchi et al. |
| 3,854,480 A | 12/1974 | Zaffaroni |
| 4,783,337 A | 11/1988 | Wong et al. |
| 5,756,115 A | 5/1998 | Moo-Young et al. |
| 5,972,372 A | 10/1999 | Saleh et al. |
| 6,004,582 A | 12/1999 | Faour et al. |
| 2002/0106410 A1 | 8/2002 | Masters |
| 2005/0276836 A1* | 12/2005 | Wilson ................ A61F 13/2051 424/422 |
| 2006/0127483 A1 | 6/2006 | Drizen et al. |
| 2006/0280795 A1* | 12/2006 | Penhasi ................ A61K 9/4891 424/472 |
| 2009/0004246 A1* | 1/2009 | Woolfson ............. A61K 9/0036 424/430 |
| 2009/0290933 A1 | 11/2009 | Skrabs |
| 2010/0285097 A1 | 11/2010 | Talling et al. |

FOREIGN PATENT DOCUMENTS

| CN | 1198091 A | 11/1998 |
| CN | 103747765 A | 4/2014 |
| EP | 2717813 | 4/2014 |
| JP | H11-512965 A | 11/1999 |
| JP | 2003-002825 A | 1/2003 |
| JP | 2003-509354 A | 3/2003 |
| JP | 2004-517674 A | 6/2004 |
| JP | 2005535558 A | 11/2005 |
| JP | 2007126478 A | 5/2007 |
| JP | 2010504484 A | 2/2010 |
| JP | 2014-520111 A | 8/2014 |
| KR | 10-2014-0037194 A | 3/2014 |
| WO | 98/04220 A1 | 2/1998 |
| WO | 03/026616 A1 | 9/2002 |
| WO | 2010069141 A1 | 6/2010 |
| WO | 2010146591 A2 | 12/2010 |
| WO | 2012170578 A1 | 12/2012 |

OTHER PUBLICATIONS

PCT/US2012/041159 International Search Report and Written Opinion dated Oct. 26, 2012; 6 pages.
PCT/US2012/041159 International Preliminary Report on Patentability dated Dec. 10, 2013; 5 pages.
European Application No. 12796540.8 Extended Search Report dated Oct. 7, 2014; 9 pages.
Patent Examination Report No. 1 for AU2012268068 on behalf of Oak Crest Institute of Science, dated Oct. 16, 2015. 3 pages.
Notice of Acceptance for AU2012268068 on behalf of Oak Crest Institute of Science, dated Sep. 28, 2016. 2 pages.
Reply to the Written Opinion prepared by the EPO for EP12796540.8 on behalf of Oak Crest Institute of Science, dated Apr. 30, 2015. 3 pages.
First Office Action for CN201280038214.7 on behalf of Oak Crest Institute of Science, dated Dec. 2, 2014. 7 pages.
The Second Office Action for CN201280038214.7 on behalf of Oak Crest Institute of Science, dated Aug. 5, 2015. 5 pages.
Notification to Grant Patent Right for Invention for CN201280038214.7 on behalf of Oak Crest Institute of Science, dated Dec. 20, 2015. 2 pages.

(Continued)

*Primary Examiner* — Johann R Richter
*Assistant Examiner* — Courtney A Brown
(74) *Attorney, Agent, or Firm* — Steinfl + Bruno LLP

(57) ABSTRACT

The present invention provides for a drug delivery device. The device can comprise at least one core with a first active pharmaceutical ingredient (API), coated with a first layer that is permeable or semi-permeable to the API, coated with a second layer that is impermeable to the API, and having a delivery window to allow passage of the API through the device and into body fluids or tissues. The device can also have a wicking material to modify the rate of transport of the API into the body fluid or tissues.

25 Claims, 16 Drawing Sheets

(56) References Cited

OTHER PUBLICATIONS

Notification of Reasons for Refusal for JP2014-514605 on behalf of Oak Crest Institute of Science, dated Feb. 9, 2016. 4 pages.
Written Amendment (translated) for JP2014-514605 on behalf of Oak Crest Institute of Science, dated Aug. 9, 2016. 4 pages.
Decision for Grant a Patent for JP2014-514605 on behalf of Oak Crest Institute of Science, dated Oct. 29, 2016. 2 pages.

* cited by examiner

A

B (A) 63.5 kDa PVA; acrylation: 10% (theoretical), 8.8% (calculated)

(B) 18 kDa PVA; acrylation: 10% (theoretical), 12.5% (calculated)

DRUG DELIVERY DEVICE EMPLOYING WICKING RELEASE WINDOW

FIELD OF INVENTION

This invention relates to drug delivery devices and therapeutic treatment using the devices.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Intravaginal rings, sub-dermal implants, and pessaries/suppositories are routinely used for the delivery of drugs both topically and systemically to vaginal or rectal tissue. Typically, these devices are made from a polymer matrix such as silicone, and the drug is dispersed throughout the matrix. Release of the drug occurs by diffusion of the drug molecules through the polymer matrix and partitioning into the fluid in the area of the body where the device is placed (e.g., in the vaginal fluid for an intravaginal ring). Two examples of matrix release devices are the intravaginal ring products Nuvaring, for the delivery of contraceptive hormones, and Estring, for the delivery of estradiol for hormone replacement therapy in menopausal women. Matrix devices provide limited control of drug release rate because the release is controlled exclusively by two factors: the relative partitioning of the drug between the polymer matrix material and the fluid into which it is released, and the diffusional characteristics of the drug within the polymer matrix. Accordingly, there exists a need in the art for drug delivery devices that allow for more control over the release of the drugs.

SUMMARY OF THE INVENTION

The following embodiments and aspects thereof are described and illustrated in conjunction with compositions and methods which are meant to be exemplary and illustrative, not limiting in scope.

Various embodiments provide for a drug delivery device, comprising at least one core comprising a first active pharmaceutical ingredient ("API"); a first coating layer that is permeable and/or semi-permeable to the API covering at least a portion of the at least one core; a second coating layer that is impermeable to the API, covering at least a portion of the first coating layer; and a delivery window to provide passage of the API through the second coating layer.

In various embodiments, the drug delivery device can comprise at least two cores, wherein a first core of the at least two core comprises the first API, and a second core of the at least two cores comprises a second API.

In various embodiments, the at least one core comprises a second API.

In various embodiments, the drug delivery device can further comprise a wicking material to modify the rate of transport of the API through the delivery window.

In various embodiments, the delivery window can be completely filled by the wicking material. In various embodiments, the delivery window can be partially filled by the wicking material.

In various embodiments, the wicking material can be positioned through the delivery window passage. In various embodiments, the wicking material can coat one or more inside walls of the delivery window. In various embodiments, the wicking material can be chemically bound to at least a portion of the second coating layer.

In various embodiments, the drug delivery device can further comprise a third coating layer between the first coating layer and the second coating layer, the third coating layer covering at least a portion of the first coating layer to slow the release of the API.

In various embodiments, the first coating layer can comprise polylactic acid polymer, polyvinyl alcohol, or combinations thereof. In various embodiments, the second coating layer can be selected from the group consisting of silicone, polyethylene ("PE"), ethylene vinyl acetate ("EVA") and combinations thereof.

In various embodiments, the wicking material can comprise a hydrophilic polymer or a fiber material. In various embodiments, the fiber material can be selected from the group consisting of silk, cotton, Nafion and combinations thereof. In various embodiments, the wicking material can comprise carboxymethylcellulose-hydroxyethylcellulose ("CMC-HEC") copolymer. In various embodiments, the wicking material can comprise polyvinylalcohol-acrylate ("PVA-MA") copolymer. In various embodiments, the wicking material can comprise polyethylene glycol-methacrylate copolymer.

In various embodiments, the drug delivery device can be configured as an intravaginal ring, a diaphragm, a pessary, a suppository, or a punctual plug. In various embodiments, the drug delivery device configured as an intravaginal ring wherein the API comprises tenofovir.

Various embodiments of the present invention provides for a method, comprising: providing a drug delivery device of the present invention; and administering the drug delivery device into a subject in need thereof to deliver the active pharmaceutical ingredient.

In various embodiments, a disease condition is treated or reduced.

In various embodiments, the disease condition can be selected from the group consisting of vaginal, uterine, pelvic, rectal, eye, ear, sinus, nasal, prostatic, and bladder.

In various embodiments, the disease condition can be selected from the group consisting of hyperhomocysteinemia, chronic renal failure, end stage renal disease, hemodialysis, peritoneal dialysis, vascular dementia, cardiovascular disease, stroke, cerebrovascular accidents, thrombotic disorder, hypercoagulable states, venous thrombosis, deep vein thrombosis, thrombophlebitis, thromboembolic disease, ischemic stroke, restenosis after percutaneous transluminal coronary angioplasty (PTCA), preeclampsia, vasculitis, digital ischemia, multifocal osteonecrosis, retinal vein occlusion, glaucoma, miscarriage, pregnancy complication, placental abruption, transplantation, diabetic retinopathy, ischemic bowel disease, cerebral vein thrombosis, atherosclerosis, coronary artery disease, penile venous thrombosis, impotence, central venous thrombosis, peripheral artery disease, intermittent claudication, hemorrhagic colitis, radiation enteritis, radiation colitis, visceral ischemia, acute mesenteric ischemia, chronic mesenteric ischemia, hypertension, microangiopathy, macroangiopathy, recurrent leg ulcer, carotid stenosis, occlusive vascular disease, arterial aneurysm, abdominal aortic aneurysm, congestive heart failure, hepatopulmonary syndrome, high flow state associated with chronic liver disease, migraine headache, vascular headache, dizziness, lightheadedness, orthostatic intolerance, postural hypotension, postural hypotension, postural orthostatic tachycardia syndrome, idiopathic pulmonary fibrosis, pulmonary hypertension, angioedema, vaso-vagal faints, neuroleptic malignant syndrome, learning disorder, learning disability, insomnia, dementia, age associated memory impairment, attention deficit/hyperactivity disorder (ADHD), mild cognitive impairment, Alzheimer's disease, Down's syndrome, autism, Parkinson's disease, depression, anxiety or anxiety disorder, Asperger syndrome, glucose intolerance, diabetes, reactive hypoglycemia, metabolic syndrome, low cortisol, hypothalamus-pituitary-adrenal dysfunction, myasthenia gravis syndrome, osteoporosis, autoimmune polyendocrine syndrome, chronic fatigue syndrome (CFS), central sensitivity syndrome, angina, syndrome X, chronic neck pain syndrome, chronic neuromuscular pain, osteoarthritis, muscle tension headache, chronic headache, cluster headache, temporalis tendonitis, sinusitis, atypical facial pain, trigeminal neuralgia, facial and neck pain syndrome, temperomandibular joint syndrome, idiopathic chronic low back pain, endometriosis, painful abdominal adhesions, chronic abdominal pain syndrome, coccydynia, pelvic floor myalgia (levator ani spasm), polymyositis, postherpetic neuralgia, polyradiculoneuropathies, mononeuritis multiplex, reflex sympathetic dystrophy, neuropathic pain, vulvar vestibulitis, vulvodynia, chronic regional pain syndrome, osteoarthritis, fibrositis, chronic visceral pain syndrome, female urethral syndrome, painful diverticular disease, functional dyspepsia, nonulcer dyspepsia, non-erosive esophageal reflux disease, acid-sensitive esophagus, interstitial cystitis, chronic pelvic pain syndrome, chronic urethral syndrome, chronic prostatitis, primary dysmenorrheal, dyspareunia, premenstrual syndrome (PMS), vulvodynia, ovarian remnant syndrome, ovulatory pain, pelvic congestion syndrome, myofasical pain syndrome, fibromyalgia polymyalgia rheumatica, Reiter's syndrome (reactive arthritis), rheumatoid arthritis, spondyloarthropathy, functional somatic syndromes, chronic regional pain syndromes, postpolio syndrome, functional somatic syndrome, rhinitis, asthma, multiple chemical sensitivity syndrome, reactive airway dysfunction syndrome, dysnomia, sick building syndrome, asthma, idiopathic pulmonary fibrosis, idiopathic pulmonary hypertension, dysphagia, gastroparesis, functional diarrhea, chronic constipation, defecation dysfunction, dysuria, atonic bladder, neurogenic bladder, irritable bowel syndrome (IBS), ileus, chronic idiopathic pseudoobstruction, Ogilvie's syndrome, restless leg syndrome, immune dysfunction syndrome, multiple sclerosis (MS), eczema, psoriasis, atopic dermatitis, dermatitis, Crohn's disease, ulcerative colitis, ulcerative proctitis, pouchitis, nonspecific ulcerative colitis, inflammatory bowel disease (IBD), celiac disease, diversion colitis, collagenous colitis, lymphocytic colitis, blind loop syndrome, nonalcoholic steatohepatitis (NASH), fatty liver, chronic liver disease, cirrhosis, spontaneous bacterial peritonitis, postoperative ileus, systemic lupus erythematosis, mixed connective tissue disorder, undifferentiated connective tissue disorder, Raynaud's phenomenon, Kawasaki syndrome, polymyositis, dermatomyositis, myositis, multiple autoimmune syndrome, Sjögren's syndrome, lichen planus, idiopathic uveitis, gingivitis, stomatitis, otitis, necrotizing enterocolitis, intensive care unit (ICU) multiple organ failure, primary biliary cirrhosis, idiopathic myelofibrosis, polyarteritis nodosa, eosinophilic pleural effusion, eosinophilic gastroenteritis, eosinophilic esophagitis, graft vs. host disease, Grave's disease, idiopathic thyroid failure, Hashimoto's thyroiditis, autoimmune hepatitis, pancreatitis, CREST syndrome, autoimmune cholangitis, ankylosing spondylitis, atopic dermatitis, vitiligo, scleroderma, autoimmune ear disease, polyangiitis overlap syndrome, primary sclerosing cholangitis, Gulf War syndrome, myalgic encephalomyelitis, food sensitivity, dysregulation spectrum syndrome, post-traumatic stress disorder (PTSD), benign tumor, malignant tumor, cancer and combinations thereof.

In various embodiments, the active pharmaceutical ingredient in the drug delivery device of the present invention can be selected from the group consisting of atazanavir, didanosine, efavirenz, emtricitabine, lamivudine, lopinavir, nevirapine, raltegravir, ritonavir, saquinavir, stavudine, tenofovir, tenofovir disoproxil fumarate, zidovudine, acyclovir, famciclovir, valcyclovir, morphine, buprenorphine, estrogen, progestin, progesterone, cyclosporine, a calcineurin inhibitor, prostaglandin, a beta-blocker, gentamycin, corticosteroid, a fluoroquinolone, insulin, an antineoplastic drug, antinausea drug, a corticosteroid, an antibiotic, morphine buprenorphine, a VEGF inhibitor, and combinations thereof.

In various embodiments, the drug delivery device can be adapted for a route of administration selected from the group consisting of: sub-dermal, sub-cutaneous, systemic, local, epidural, intra-lesional, intra-tumor, intra-punctal and combinations thereof.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
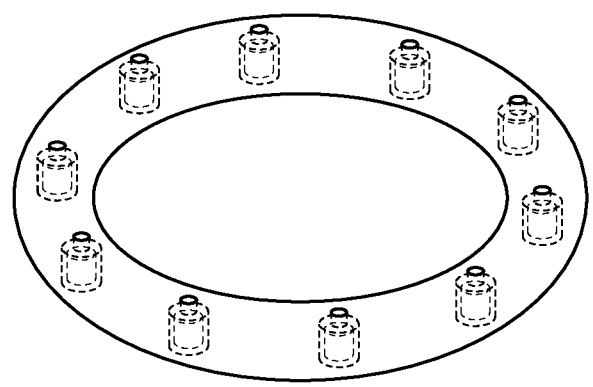
FIG. 1 depicts a delivery device in accordance with various embodiments of the present invention. (A) A drawing of the delivery device in intravaginal ring configuration. There are ten API pods, each with a separate delivery window. (B) Cross-sectional view of a single API pod in A showing the API core (101), permeable and/or semi-permeable polymer coating (102), and impermeable outer coating (103) with delivery window (104). No wicking material is shown in the delivery window or API cavity.
Figure 1:
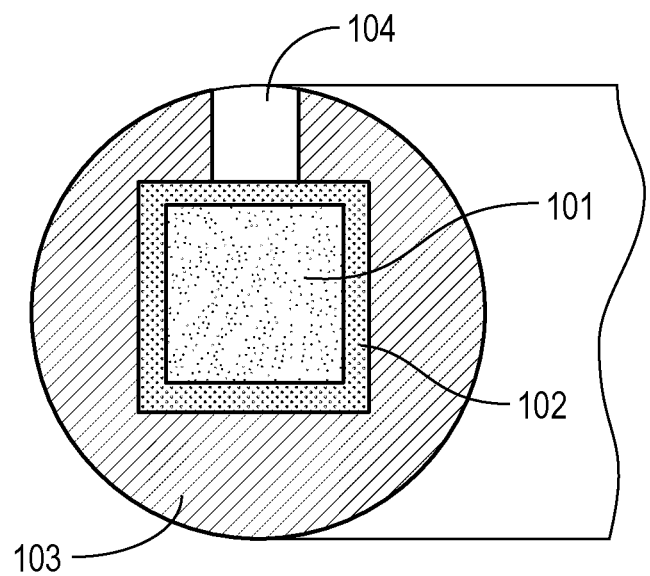

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"API" as used herein refers to active pharmaceutical ingredient.

"Core" as used herein relating to the drug delivery device refers to a formed (e.g., pressed) API composition (e.g., tablet) that is uncoated.

"Pod" as used herein refers a core (e.g., uncoated, formed API tablet) coated with one or more layers of biocompatible polymers, but without a final sealing polymer layer and/or delivery channel.

"Drug delivery device" as used herein with respect to the present invention refers to a device comprising one or more pods, a sealing polymer layer and/or one or more delivery channels. The drug delivery device is intended to be used either internally or externally to administer a pharmaceutical drug compound in a controlled manner (controlled dosing rate and total dose).

"CMCNa" as used herein refers to carboxymethylcellulose, sodium salt.

"dH$_2$O" as used herein refers to deionized water.

"DVS" as used herein refers to divinylsulfone, a cross-linking agent.

"EVA" as used herein refers to ethylenevinylacetate.

"FTIR" as used herein refers to Fourier transform infrared spectroscopy.

"HEC" as used herein refers to hydroxyethylcellulose.

"Excipient" as used herein refers to pharmaceutically inactive components included in the drug delivery device. Excipients can include but are not limited to dyes, flavors, binders, emollients, fillers, lubricants, and preservatives. Excipients can be used to modify the release or other characteristics of the API; for example, increasing the solubility of the API, or they may be inactive, such as fillers and colorings.

"Impermeable" as used herein in reference to a coating layer refers to a layer that will not allow passage of the effective agent at a rate required to obtain the desired local or systemic physiological or pharmacological effect.

"Semi-permeable" as used herein in reference to a coating layer refers to a layer that will allow passage of the effective agent, but at a rate significantly slower than if there were no polymer or a release polymer present.

"Significantly slower" as used herein refers to a rate 0.5- to 5-$\log_{10}$ units slower.

"IVR" as used herein refers to intravaginal ring delivery device.

"LSR" as used herein refers to liquid silicone resin.

"NMR" as used herein refers to nuclear magnetic resonance spectroscopy. $^1$H-NMR as used herein refers to proton NMR spectroscopy.

"Optional" or "optionally" as used herein means that a described event or circumstance may or may not occur, and that the description includes instances where said event or circumstance occurs and instances in which it does not. For example, "optionally coated with a blocking polymer" means that a blocking polymer may or may not be used in the formulation, and that the description includes both the case where a blocking polymer is present, and the case where it is omitted.

"PE" as used herein refers to polyethylene.

"PLA" as used herein refers to polylactic acid polymer, also referred to as polylactide, comprised of poly-L-lactide, poly-D-lactide, or poly-D,L-lactide.

"PVA" as used herein refers to polyvinylalcohol polymer.

"PVA-MA" as used herein refers topolyvinylalcohol-methacrylate copolymer polymer.

"TFV" as used herein refers to tenofovir, an antiretroviral microbicide drug.

The disclosed invention is a drug delivery device that utilizes a unique combination of permeable and semi-permeable polymer coatings, release window size and number in nonpermeable polymer coatings and/or structures, and hydrogel or wicking materials to precisely control the release of a desired API into a human patient. In various embodiments, the delivery device may be an insert such as an intravaginal ring, diaphragm, pessary, or suppository.

Drug release from the delivery devices disclosed herein may be controlled by multiple factors, including the solubility of the drug in the release fluid, the polymer coatings applied to the drug core, the size and quantity of delivery window channels exposing the drug core to the release fluid, and the characteristics of any wicking materials applied within the drug cavity and/or delivery channels.

FIG. 1 illustrates an embodiment of the present invention. While the device shown in FIG. 1 is configured as a ring, the device can be any shape. FIG. 1A shows the delivery device in an intravaginal ring configuration with ten API pods, each connected to a separate delivery window. FIG. 1B shows the device comprising a core of an API 101, a first coating layer 102 that is permeable and/or semi-permeable to the API covering the core, a second coating layer 103 that is impermeable to the API covering the first coating layer, and a delivery window 104 to provide passage of the API through the second coating.

Figure 2:
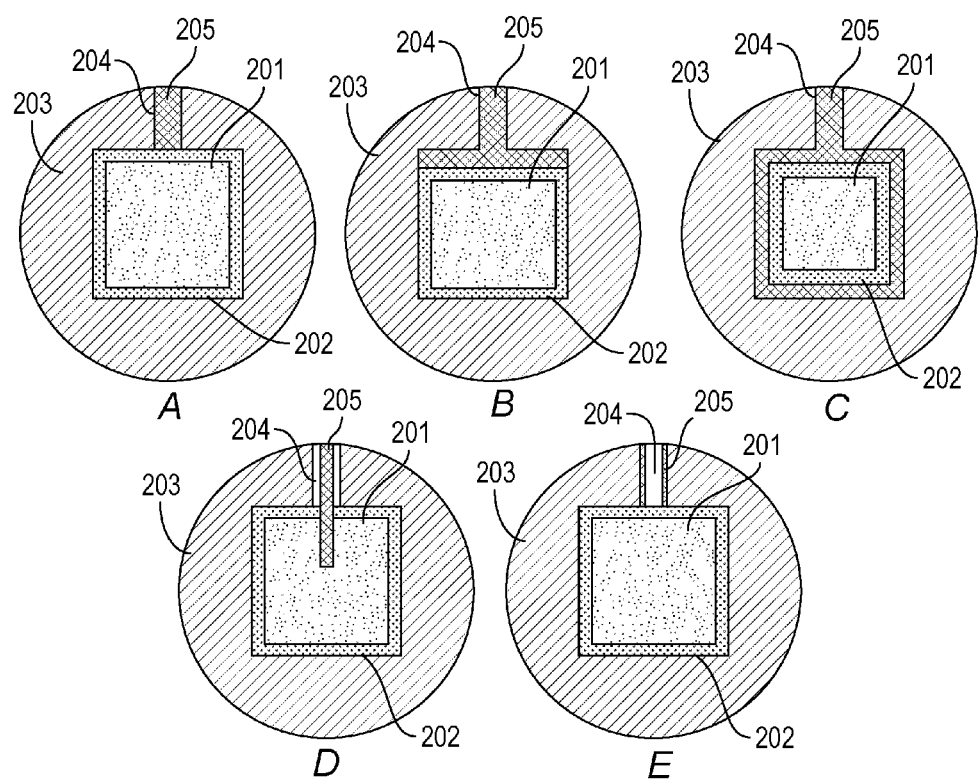
FIG. 2 depicts a delivery device in accordance with various embodiments of the present invention. Cross-sectional views of possible delivery device configurations: 203 is silicone, EVA, or other impermeable material that forms the outer shell of the device containing the delivery window; 201 represents the solid API core; 202 the permeable and semi-permeable polymer coating layer or layers; 204 represents the delivery window; and 205 the hydrogel or other wicking material. Five configurations are shown: (a) wick material filling only the delivery window; (b) wick material fills the delivery window and top of the API pod cavity; (c) wick material fills the delivery window and completely surrounds the API pod; (d) wick extends through the delivery window and into the API pod; (e) the wick material coats the walls of the delivery window but does not completely fill the window space. This coating may extend into the API pod cavity as well.

FIG. 2 shows various embodiments of the device including a wicking material 205, in addition to a core 201 comprising an API, a first coating layer 202 that is permeable and/or semi-permeable to the API covering the core, a second coating layer 203 that is impermeable to the API covering the first coating layer, and a delivery window 204 to provide passage of the API through the second coating. FIG. 2A shows the wicking material 205 filling the delivery window 204. FIG. 2B shows the wicking material 205 filling the delivery window 204 and the top of the first coating layer 202. FIG. 2C shows the wicking material 205 filling the delivery window 204 and completely surrounding the first coating layer 202. FIG. 2D shows the wicking material 205 extending through the delivery window 204 and into the core 201. FIG. 2E shows the wicking material 205 coating the interior walls of the delivery window 204.

Figure 3:
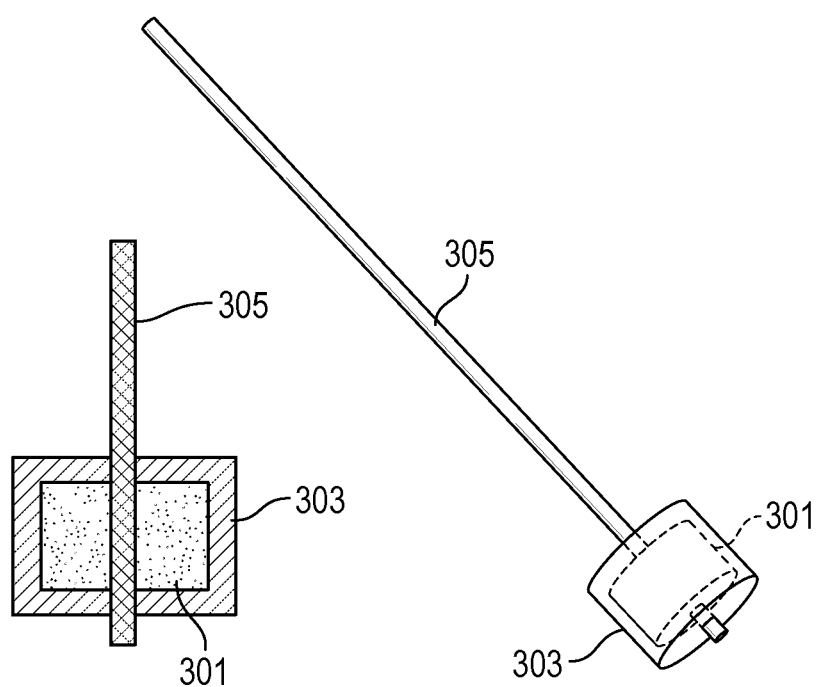
FIG. 3 depicts a delivery device in accordance with various embodiments of the present invention. Delivery device comprises a compressed API pod (301) coated with an impermeable shell of silicone (303). A fiber wick (in this case a silk suture 305; in other embodiments, the wick can also be a biodegradable polymer) penetrates the core and serves as both a delivery channel for the drug to pass through the silicone shell and a suture to hold the device in place (for example in the eye).

FIG. 3 shows an embodiment of the device. The core 301 comprising the API is surrounded by an impermeable shell of silicone 303, and a silk suture 305 penetrates the core 301 and serves as both a delivery channel for the drug to pass through the impermeable shell 303 and a suture to hold the device in place.

Figure 6:
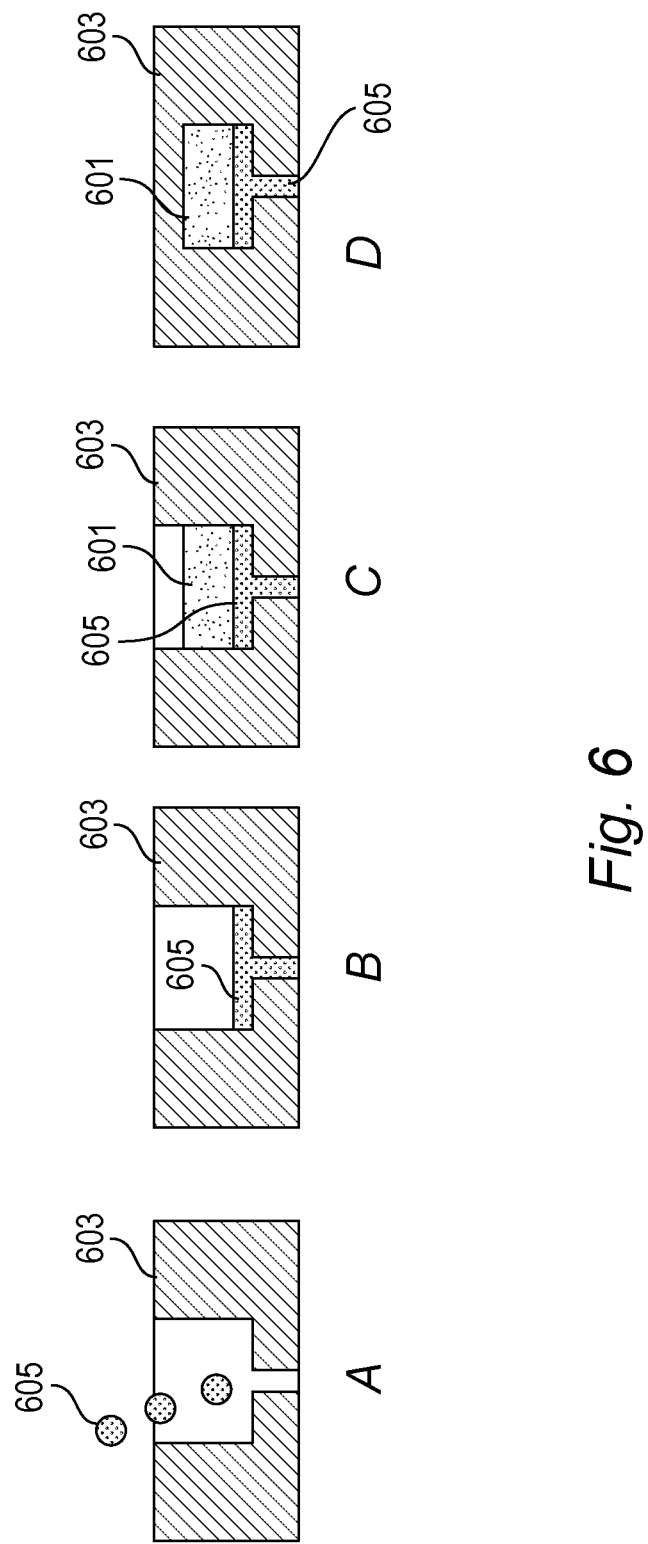
FIG. 6 depicts a method for incorporation of CMC-HEC into IVRs in accordance with various embodiments of the present invention. (A) CMC-HEC polymer solution (605) added to pod cavity, (B) CMC-HEC (605) allowed cure 24 h, (C) TFV pod (601) inserted in cavity, (D) cavity sealed with silicone (603).

FIG. 6 shows an example of a method for incorporating CMC-HEC (i.e., wicking material) into the device. FIG. 6A shows the CMC-HEC polymer solution 605 added to the pod cavity; FIG. 6B shows the CMC-HEC polymer solution 605 curing for a 24 hour period; FIG. 6C shows the core 601 comprising the API inserted into the cavity; and FIG. 6D shows the cavity sealed with silicone 603 (impermeable coating).

Various embodiments of the present invention provide for a drug delivery device with a solid core of API coated with polymer layers to control drug dissolution and subsequent release rate. In various embodiments, one polymer layer is a release polymer that is permeable to the API of interest (this forms the API "pod"). In various embodiments, the outer layer is a sealing material such as silicone, polyethylene (PE), or ethylene vinyl acetate (EVA).

In various embodiments, there is an optional "blocking polymer" layer between the release polymer and outer sealing layer, coating some or all of the "pod" surface to provide for slow release of API. In various embodiments, the blocking polymer is made of the same material as the impermeable layer. In other embodiments, the blocking polymer is made of a different material than the impermeable layer.

Materials that may be suitable for fabricating the coating layers of the device include naturally occurring or synthetic materials that are biologically compatible with body fluids and tissues.

Naturally occurring or synthetic materials that are biologically compatible with body fluids and tissues and essentially insoluble in body fluids which the material will come in contact include, but are not limited to, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinyl formal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumerale copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitride copolymer, hydroxypropylmethylcellulose polymer, and ethylcellulose polymer.

Specifically, the release polymer of the device of the present invention may be made of any of the above-listed polymers or any other polymer which is biologically compatible with body fluids and tissues, essentially insoluble in body fluids which the material will come in contact and permeable to the passage of the effective drug agent. Agents coated with a layer of release polymer require either a blocking polymer layer or a sealing layer and delivery channel to be present in order to allow passage of the agent at a rate required to obtain the desired local or systemic physiological or pharmacological effect. The blocking polymer of the device of the present invention may be made of any of the above-listed polymers or any other polymer which is biologically compatible with body fluids and tissues, is essentially insoluble in body fluids which the material will come in contact, and which is essentially impermeable or semi-permeable to the passage of the effective agent. The term impermeable, as used herein, means that the layer will not allow passage of the effective agent at a rate required to obtain the desired local or systemic physiological or pharmacological effect. The term semipermeable means that the layer will allow passage of the effective agent, but at a rate significantly slower than if there were no polymer or a release polymer present. The behavior of any given polymer material as permeable, semipermeable, or impermeable (i.e. release, blocking, or sealing polymer) is dependent on the properties of the drug, including but not limited to solubility, hydrophobicity, hydrophilicity or lipophilicity, and log p (octanol-water partitioning coefficient).

In various embodiments, the sealing (silicone, EVA, PE) layer forms the body of an intravaginal ring, diaphragm, intrauterine device, or other medical implant. There may be one or more "pods" in a single ring or device. The sealing layer contains a delivery window that is a passage through the sealing layer to the API pod, allowing release of API from the device by diffusion through the delivery window space. There may be a single window or multiple windows for each pod. (FIG. 1). In various embodiments, the delivery window is filled by a wicking material to modify the rate of transport of fluid and/or API through the window space. Depending on the wicking material and application, the rate of transport can be increased or decreased. A number of these possible configurations are shown in FIG. 2. In various embodiments, the wick may be a hydrophilic polymer (hydrogel). Examples of such a hydrogel material include, but are not limited to, a hydroxyethylcellulose-carboxymethylcellulose copolymer, polyvinyl alcohol-methacrylate copolymer, or polyethylene glycol-methacrylate copolymer. In various embodiments, the wick can be a fiber material or bundle of fibers. Examples include: silk, cotton, and Nafion. FIG. 3 shows a device of this configuration. In various embodiments, the wick can completely fill the delivery window space, or it may only partially fill the window. Partial filling can be in the center of the window passage (such as a fiber penetrating the window), or it can be a wicking polymer coating on the delivery window inside walls. The wicking material can also be chemically bound to the silicone material as opposed to simply coating the surface. An example of this would be modification of the exposed silanol (Si—OH) functionalities on the delivery window walls using a poly(ethylene glycol) cross-linked polymer to improve surface wetting. In various embodiments, the hydrogel material, besides filling the delivery window, may also partially fill the drug pod cavity, providing a hydrogel layer completely surrounding, or partially surrounding, the API pod.

A large number of polymers can be used to construct the devices of the present invention. The requirements are that they are inert, non-immunogenic and of the desired permeability.

The impermeable layer of the device of the present invention may be made of appropriate impermeable members of above-listed polymers, preferably silicone, ethylene vinylacetate copolymer, or polyethylene, or any other polymer which is biologically compatible with body fluids and tissues and essentially impermeable to the passage of the effective agent.

The permeable and/or semi-permeable layer of the device of the present invention must be biologically compatible with body fluids and tissues and permeable to the passage of the agent or composition effective in obtaining the desired effect.

The effective agent diffuses in the direction of lower chemical potential, i.e., toward the exterior surface of the device. At the exterior surface of the device, equilibrium is again established. When the conditions on both sides of the permeable and/or semi-permeable coating layer are maintained constant, a steady state flux of the effective agent will be established in accordance with Fick's Law of Diffusion. The rate of passage of the drug through the material by diffusion is generally dependent on the solubility of the drug therein, as well as on the thickness of the wall, among other parameters (see below). This means that selection of appropriate materials for fabricating the wall will be dependent on the particular drug to be used.

The rate of diffusion of the effective agent through a polymeric layer of the present invention may be determined via diffusion cell studies carried out under sink conditions. In diffusion cell studies carried out under sink conditions, the concentration of drug in the receptor compartment is essentially zero when compared to the high concentration in the donor compartment. Under these conditions, the rate of drug release is given by:

$$\frac{Q}{t} = \frac{D \times K \times A \times DC}{h}$$

where Q is the amount of drug released, t is time, D is the diffusion coefficient, K is the partition coefficient, A is the surface area, DC is the difference in concentration of the drug across the membrane, and h is the thickness of the membrane.

In the case where the agent diffuses through the layer via water filled pores, there is no partitioning phenomena. Thus, K can be eliminated from the equation. Under sink conditions, if release from the donor side is very slow, the value DC is essentially constant and equal to the concentration of the donor compartment. Release rate therefore becomes dependent on the surface area (A), thickness (h) and diffusivity (D) of the membrane. In the construction of the device of the present invention, the size (and therefore, surface area) is mainly dependent on the size of the effective agent.

Thus, permeability values may be obtained from the slopes of a Q versus time plot. The permeability P, can be related to the diffusion coefficient D, by:

$$P = \frac{K \times D}{h}$$

Exemplary microporous materials suitable for use as a permeable and/or semi-permeable coating layer, for instance, are described in U.S. Pat. No. 4,014,335 which is incorporated herein by reference in its entirety. These materials include cross-linked polyvinyl alcohol, polyolefins or polyvinyl chlorides or cross-linked gelatins; regenerated, insoluble, nonerodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen. Polylactic acid or cross-linked polyvinyl alcohol is preferred. The permeable and/or semi-permeable coating layer is selected so as to slow release of the agent from the inner core into contact with a mammalian organism, e.g., a human. The permeable and/or semi-permeable coating layer need not provide gradual release or control of the agent into the biological environment, however, the permeable and/or semi-permeable coating layer may be advantageously selected to also have that property or feature.

The devices of the present invention may be made in a wide variety of ways, such as by obtaining an effective amount of the API and compressing the API to a core of the desired shape. For example, once shaped, a permeable/semi-permeable and/or impermeable coating layer may be applied to the API core creating a coated API pod. In the case of the ethylene vinyl acetate, the impermeable coating layer may be applied directly in the form of a sheet or membrane to the outer surface of the pod. In various embodiments, the API core may have a permeable coating applied to its entire surface prior to coating with the impermeable coating layer. In the case of polylactic acid or polyvinyl alcohol, the permeable and/or semi-permeable coating may be applied by dipping the API core or pod one or more times in a solution containing the desired polymer. Optionally, the permeable and/or semi-permeable coating layer may be applied by dropping, spraying, brushing or other means of coating the outer surface of the core or pod with the polymer solution. For permeable/semipermeable coatings applied to the entire core surface, a preferable method for coating is spray-coating in a fluidized-bed or pan coating device. When using a polylactic acid or polyvinyl alcohol solution to obtain the permeable and/or semi-permeable coating layer, the desired thickness may be obtained by applying several coats. Each coat may be dried prior to applying the next coat.

The following are non-limiting examples of classes of agents can be incorporated into the devices of the present invention as the API:
1) anesthetics and pain killing agents (e.g., lidocaine and related compounds, benzodiazepam and related compounds, and buprenorphine and related compounds);
2) antiallergenics (e.g., antazoline, methapyriline, chlorpheniramine, pyrilamine and prophenpyridamine);
3) antibiotics [e.g., aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole]; particular antibiotics include, but are not limited to tetracycline, chlortetracycline, bacitracin, neomycin, polymyxin, gramicidin, oxytetracycline, chloramphenicol, gentamycin, and erythromycin);
4) antibacterial (e.g., sulfonamides, sulfacetamide, sulfamethizole, sulfisoxazole, nitrofurazone and sodium propionate);
5) anticancer or antineoplastic agents (e.g., chemotherapeutic agents and antiproliferative agents)
Examples of chemotherapeutic agents include cytotoxic agents (e.g., 5-fluorouracil, cisplatin, carboplatin, methotrexate, daunorubicin, doxorubicin (Adriamycin®), vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).
Examples of antiproliferative agents include alkylating agents, antimetabolites, enzymes, biological response modifiers, hormones and antagonists, androgen inhibitors (e.g., flutamide and leuprolide acetate), antiestrogens (e.g., tamoxifen citrate and analogs thereof, toremifene, droloxifene and roloxifene); additional examples of antiproliferative agents include, but are not limited to levamisole, gallium nitrate, granisetron, sargramostim strontium-89 chloride, filgrastim, pilocarpine, dexrazoxane, and ondansetron.

Specific anti-cancer agents include but are not limited to 5-fluorouracil, adriamycin and related compounds.

6) anti-inflammatory agents (e.g., hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone, 6-mannose phosphate);
7) anti-fungal agents (e.g., fluconazole and related compounds);
8) antiviral agents (e.g., acyclovir and related agents, tenofovir, maraviroc, emtricitabine, saquinavir, idoxuridine, trisodium phosphomonoformate, trifluorothymidine, ganciclovir, DDI and AZT);
9) cell transport/mobility impending agents (e.g., colchicine, vincristine, cytochalasin B and related compounds);
10) Beta-blockers: (e.g., timolol, betaxolol atenolol, etc.);
11) Prostaglandins (e.g., latanaprost)
12) decongestants (e.g., phenylephrine, naphazoline, and tetrahydrazoline);
13) HIV drugs (e.g., NNRTI, NRTI, protease inhibitor, entry inhibitor);
14) hormones (e.g., for contraception);
15) hormones (e.g., for hormone replacement therapy);
16) hormones (e.g., for infertility, assisted reproductive therapy (ART), and in vitro fertilization (IVF))
17) immunological response modifiers (e.g., muramyl dipeptide and related compounds);
18) miotics and anti-cholinesterase (e.g., pilocarpine, eserine salicylate, carbachol, di-isopropyl fluorophosphate, phospholine iodine, and demecarium bromide);
19) mydriatics (e.g., afropine sulfate, cyclopentolate, homatropine, scopolamine, tropicamide, eucatropine, and hydroxyamphetamine);
20) peptides and proteins (e.g., cyclosporin, insulin, growth hormones, insulin related growth factor, heat shock proteins, antibodies and related compounds);
21) steroidal compounds (e.g., dexamethasone, prednisolone and related compounds);
22) sympathomimetics (e.g., epinephrine);
23) carbonic anhydrize inhibitors;
24) agents to treat incontinence; and
25) agents commonly used in topical therapy, (e.g., lactic acid for the vaginal tract);
26) agents that act on the sympathetic and/or parasympathetic nervous systems;
27) antipsychotics; and
28) antidepressants.

Reference may be made to any standard pharmaceutical textbook such as Remington's Pharmaceutical Sciences for the identity of other agents. Any pharmaceutically acceptable form of such a compound may be employed in the practice of the present invention; e.g., the free base, a pharmaceutically acceptable salt or derivative thereof (e.g., ester, carbamate, amide). Pharmaceutically acceptable salts, for instance, include sulfate, lactate, acetate, stearate, hydrochloride, tartrate, maleate and the like.

Various embodiments of the invention also provide for a method of treating a subject in need thereof to obtain a desired local or systemic physiological or pharmacological effect from an API. The method can comprise providing a drug delivery device of the present invention; and administering the drug delivery device to the subject and allowing the API to pass through the delivery window of the drug delivery device to contact the subject. Administering can include, but not limited to, positioning, inserting, injecting, implanting, or any other methods for exposing the drug delivery device to the subject.

The drug delivery device of the present invention can also be administered to a mammalian organism via any route of administration known in the art. Such routes of administration include intraocular, oral, subcutaneous, intramuscular, intraperitoneal, intranasal, dermal, and the like. In addition, one or more of the devices may be administered at one time or more than one agent may be included in the inner core.

These methods of administration and technique for their preparation are well known by those of ordinary skill in the art. Techniques for their preparation can be found in Remington's Pharmaceutical Sciences.

The drug delivery system may be administered for a sufficient period of time and under conditions to allow treatment of the disease state of concern.

For localized drug delivery, the devices may be surgically implanted at, in or near the site of action. This can be the case, for example, for devices of the present invention used in treating ocular conditions, primary tumors, rheumatic and arthritic conditions, and chronic pain.

For systemic relief, the devices may be implanted subcutaneously, intramuscularly or intraperitoneally. This can be the case when devices are to give sustained systemic levels and avoid premature metabolism.

As would be readily understood by one skilled in the art, the amounts, materials and dimensions depend on the method of administration, the effective agent used, the polymers used, the desired release rate and the like. Likewise, actual release rates and release duration depend on a variety of factors in addition to the above such as the disease state being treated, the age and condition of the patient, the route of administration as well as other factors which would be readily apparent to those skilled in the art.

Particular conditions and disease conditions that are believed to be appropriate to treat in connection with various embodiments of the present invention include conditions and disease conditions related, but are in no way limited to the following categories: Hypercoagulable states related to hyperhomocysteinemia (e.g., hyperhomocysteinemia, chronic renal failure, end stage renal disease, hemodialysis, peritoneal dialysis, vascular dementia, cardiovascular disease, stroke, cerebrovascular accidents, thrombotic disorder, hypercoagulable states, venous thrombosis, deep vein thrombosis, thrombophlebitis, thromboembolic disease, ischemic stroke, restenosis after percutaneous transluminal coronary angioplasty (PTCA), preeclampsia, vasculitis, digital ischemia, multifocal osteonecrosis, retinal vein occlusion, glaucoma, miscarriage, pregnancy complication, placental abruption, transplantation, diabetic retinopathy, ischemic bowel disease, cerebral vein thrombosis, atherosclerosis, coronary artery disease, penile venous thrombosis, impotence, central venous thrombosis, peripheral artery disease, intermittent claudication, hemorrhagic colitis, radiation enteritis and colitis, visceral ischemia, acute mesenteric ischemia, chronic mesenteric ischemia, hypertension, microangiopathy, macroangiopathy, recurrent leg ulcer, carotid stenosis, occlusive vascular disease, arterial aneurysm, abdominal aortic aneurysm); Vasodilatatory states (e.g., congestive heart failure, hepatopulmonary syndrome, high flow state associated with chronic liver disease, migraine headache, vascular headaches, dizziness, lightheadedness, orthostatic intolerance, postural hypotension, postural hypotension, postural orthostatic tachycardia syndrome, idiopathic pulmonary fibrosis, pulmonary hypertension, angioedema, vaso-vagal faints, neuroleptic malignant syndrome); Interference with function as neurotransmitter (e.g., learning disorder, learning disability, insomnia, dementia, age associated memory impairment, attention deficit/hyperactivity disorder (ADHD), mild cognitive impairment, Alzheimer's disease, Down's syndrome, autism, Parkinson's disease, depression, anxiety or anxiety disorder, Asperger syndrome); Interference with endocrine function (e.g., glucose intolerance, diabetes, reactive hypoglycemia, metabolic syndrome, low cortisol, hypothalamus-pituitary-adrenal dysfunction, myasthenia gravis syndrome, osteoporosis, autoimmune polyendocrine syndrome); Chronic pain syndromes due to stimulation of N-methyl-D-asparate (NMDA) receptors leading to hypersensitivity (e.g., chronic fatigue syndrome (CFS), central sensitivity syndrome, angina, syndrome X, chronic neck pain syndrome, chronic neuromuscular pain, osteoarthritis, muscle tension headaches, chronic headaches, cluster headache, temporalis tendonitis, sinusitis, atypical facial pain, trigeminal neuralgia, facial and neck pain syndrome, temperomandibular joint syndrome, idiopathic chronic low back pain, endometriosis, painful abdominal adhesions, chronic abdominal pain syndromes, coccydynia, pelvic floor myalgia (levator ani spasm), polymyositis, postherpetic neuralgia, polyradiculoneuropathies, mononeuritis multiplex, reflex sympathetic dystrophy, neuropathic pain, vulvar vestibulitis, vulvodynia, chronic regional pain syndrome, osteoarthritis, fibrositis, chronic visceral pain syndrome, female urethral syndrome, painful diverticular disease, functional dyspepsia, nonulcer dyspepsia, non-erosive esophageal reflux disease, acid-sensitive esophagus, interstitial cystitis, chronic pelvic pain syndrome, chronic urethral syndrome, chronic prostatitis, primary dysmenorrheal, dyspareunia, premenstrual syndrome (PMS), vulvodynia, ovarian remnant syndrome, ovulatory pain, pelvic congestion syndrome, myofasical pain syndrome, fibromyalgia polymyalgia rheumatica, Reiter's syndrome (reactive arthritis), rheumatoid arthritis, spondyloarthropathy, functional somatic syndromes, chronic regional pain syndromes, post-polio syndrome, functional somatic syndrome); Injury to nasal and respiratory tract (e.g., rhinitis, asthma, multiple chemical sensitivity syndrome, reactive airway dysfunction syndrome, dysnomia, sick building syndrome, asthma, idiopathic pulmonary fibrosis, idiopathic pulmonary hypertension); Interference with visceral smooth muscle contractile function (e.g., dysphagia, gastroparesis, functional diarrhea, chronic constipation, defecation dysfunction, dysuria, atonic bladder, neurogenic bladder, irritable bowel syndrome (IBS), ileus, chronic idiopathic pseudoobstruction, Ogilvie's syndrome); Inhibition of aerobic metabolism/ischemia disorders (e.g., restless leg syndrome, chronic fatigue syndrome); Triggering of inflammation (e.g., immune dysfunction syndrome, multiple sclerosis (MS), eczema, psoriasis, atopic dermatitis, dermatitis, Crohn's disease, ulcerative colitis, ulcerative proctitis, pouchitis, nonspecific ulcerative colitis, inflammatory bowel disease (IBD), celiac disease, diversion colitis, collagenous colitis, lymphocytic colitis, blind loop syndrome, nonalcoholic steatohepatitis (NASH), fatty liver, chronic liver disease, cirrhosis, spontaneous bacterial peritonitis, postoperative ileus, systemic lupus erythematosis, mixed connective tissue disorder, undifferentiated connective tissue disorder, Raynaud's phenomenon, Kawasaki syndrome, polymyositis, dermatomyositis, myositis, multiple autoimmune syndrome, Sjögren's syndrome, lichen planus, idiopathic uveitis, gingivitis, stomatitis, otitis, necrotizing enterocolitis, intensive care unit (ICU) multiple organ failure, primary biliary cirrhosis, idiopathic myelofibrosis, polyarteritis nodosa, eosinophilic pleural effusion, eosinophilic gastroenteritis, eosinophilic esophagitis, graft vs. host disease, Grave's disease, idiopathic thyroid failure, Hashimoto's thyroiditis, autoimmune hepatitis, pancreatitis, CREST syndrome, autoimmune cholangitis, ankylosing spondylitis, atopic dermatitis, vitiligo, scleroderma, autoimmune ear disease, polyangiitis overlap syndrome, primary sclerosing cholangitis); overlap disorders (e.g., Gulf War syndrome, myalgic encephalomyelitis, food sensitivity, dysregulation spectrum syndrome, post-traumatic stress disorder (PTSD)); interference with regulation of apoptosis and proliferation (e.g., benign tumors, malignant tumors, cancer).

The invention disclosed herein can be used in a range of anatomical compartments to treat a range of medical conditions using a range of active pharmaceutical ingredients (APIs). The following examples are intended to illustrate combinations and are not meant to be restrictive.

For use in the vagina, the device can be used for (1) treating HIV or HIV prophylaxis (e.g., reduce the likelihood of acquiring HIV) with the device having atazanavir, didanosine, efavirenz, emtricitabine, lamivudine, lopinavir, nevirapine, raltegravir, ritonavir, saquinavir, stavudine, tenofovir, tenofovir disoproxil fumarate, or zidovudine; (2) treating HSV or HSV prophylaxis (e.g., reduce the likelihood of acquiring HSV) with the device having acyclovir, famciclovir, or valcyclovir; (3) treating pelvic pain with the device having morphine or buprenorphine; (4) contraception with the device having estrogens and/or progestins; (5) hormone replacement with the device having estrogens; and (6) treating fertility with the device having progesterone.

For use in the eye, the device can be used for (1) treating dry eye with the device having cyclosporine or other calcineurin inhibitors; and (2) treating glaucoma with the device having prostaglandins or beta-blockers.

For use in the ear, the device can be used for (1) treating Meniere's disease with the device having gentamycin or corticosteroids; and (2) otitis media with the device having antibiotics such as fluoroquinolones, or with the device having corticosteroids.

For systemic treatment, the device can be used for (1) treatment of psoriasis with the device having cyclosporine; and (2) treatment of diabetes with the device having insulin.

For local treatment, the device can be used for the treatment of tumors with the device having antineoplastic drugs.

For systemic treatment, the device can have anti-nausea drugs.

For local treatment, the device can be used to treat ulcerative colitis with the device having corticosteroids.

For treatment of sinus or nasal conditions, the device can be used for (1) treatment of chronic sinusitis with the device having antibiotics or corticosteroids.

For CNS or epidural treatment, the device can be used for (1) treatment of chronic pain with analgesics such as morphine or buprenorphine.

For intra-lesional or intra-tumor (e.g., cancer) treatment, the device can have antineoplastics or VEGF inhibitors.

The device can also be adapted for rectal uses as well as sub-dermal/sub-cutaneous uses.

In various embodiments, the drug delivery device is adapted for intravaginal administration. In other embodiments, the drug delivery device is adapted for intrauterine administration. In various embodiments, the invention provides for a method for treating a mammal having or prone to a vaginal or uterine disease condition, or treating a mammal prophylactically to prevent or reduce the occurrence or severity of a vaginal or uterine disease condition, comprising providing a drug delivery device of the present invention and administering a therapeutically effective amount of an agent capable of treating the vaginal or uterine disease condition via the drug delivery device. In other embodiments, the invention provides for a method of contraception, comprising providing a drug delivery device of the present invention and administering a therapeutically effective amount of one or more contraceptive agents via the drug delivery device. In other embodiments, the invention provides for a method of hormone replacement; for example, to treat or reduce menopausal symptoms, comprising providing a drug delivery device of the present invention and administering a therapeutically effective amount of one or more hormones via the drug delivery device. In other embodiments, the invention provides for a method of treating pelvic pain, comprising providing a drug delivery device of the present invention and administering a therapeutically effective amount of one or more agents to treat pelvic pain via the drug delivery device. These methods include positioning the drug delivery device at an area wherein release of the agent is desired and allowing the agent to pass through the device to the desired area of treatment. Such devices provide sustained controlled release of various compositions to treat the vaginal or uterine disease conditions and lower the risk of detrimental local and systemic side effects.

In various embodiments, the drug delivery device is adapted for antiviral treatment. In various embodiments, the invention provides for a method for treating a mammal having or prone to a viral disease condition or treating a mammal prophylactically to prevent or reduce the occurrence or severity of a viral disease condition, comprising providing a drug delivery device of the present invention, and administering a therapeutically effective amount of an agent capable of treating the viral disease condition via the drug delivery device. The methods include positioning the drug delivery device at an area wherein release of the agent is desired and allowing the agent to pass through the device to the desired area of treatment. Such devices provide sustained controlled release of various compositions to treat the rectal disease conditions and lower the risk of detrimental local and systemic side effects.

In various embodiments, the drug delivery device is adapted for rectal administration. In various embodiments, the invention provides for a method for treating a mammal having or prone to a rectal disease condition or treating a mammal prophylactically to prevent or reduce the occurrence or severity of a rectal disease condition, comprising providing a drug delivery device of the present invention, and administering a therapeutically effective amount of an agent capable of treating the rectal disease condition via the drug delivery device. The methods include positioning the drug delivery device at an area wherein release of the agent is desired and allowing the agent to pass through the device to the desired area of treatment. Such devices provide sustained controlled release of various compositions to treat the rectal disease conditions and lower the risk of detrimental local and systemic side effects.

In various embodiments, the drug delivery device is adapted for administration at, in or near the eye. In various embodiments, the device can be implanted at, in or near the eye. In various embodiments the invention provides for a method for treating a mammal having or prone to an eye disease condition, or treating a mammal prophylactically to prevent or reduce the occurrence or severity of an eye disease condition, comprising providing a drug delivery device of the present invention, and administering a therapeutically effective amount of an agent capable of treating the eye disease condition via the drug delivery device. The method includes positioning a sustained released drug delivery system at an area wherein release of the agent is desired and allowing the agent to pass through the device to the desired area of treatment. Such devices provide sustained controlled release of various compositions to treat the eye disease condition and lower the risk of detrimental local and systemic side effects. In various embodiments, the method can involve or be configured as a punctual plug, and the API can thereby the delivered.

In various embodiments, the drug delivery device can be adapted for administration at, in or near the ear. In various embodiments, the device can be implanted at, in or near the ear. In various embodiments, the invention provides for a method for treating a mammal having or prone to a hearing (or balance) impairment or treating a mammal prophylactically to prevent or reduce the occurrence or severity of a hearing (or balance) impairment that would result from inner ear cell injury, loss, or degeneration, caused by an ototoxic agent, comprising providing a drug delivery device of the present invention, and administering a therapeutically effective amount of an otoprotective agent via the drug delivery device. The method includes positioning a sustained released drug delivery system at an area wherein release of the agent is desired and allowing the agent to pass through the device to the desired area of treatment. The invention provides a method for direct implantation of a drug delivery device in to the inner ear in the vicinity of the oval window. Such devices provide sustained controlled release of various compositions to treat the inner ear and lower the risk of detrimental local and systemic side effects. Accordingly an embodiment of the invention is a method of treating a condition of the ear of a mammal comprising the steps of accessing an internal anatomical site adjacent to the inner ear, and placing or implanting a drug delivery device in the internal anatomical site.

In particular embodiments, the present invention provides a method for treating inner ear diseases and their associated symptoms including, but not limited to, congenital abnormalities such as congenital syphilis and toxoplasmosis; viral or bacterial infections; cancers; and acquired inner ear diseases such as Meniere's disease, sensoryneuronal hearing loss or ototoxicity. Another embodiment involves maintaining the integrity or keeping cochlear hair cells intact within the inner ear. The goal is, therefore, to leave vestibular hair cells intact. Thus, it would be advantageous to administer gentamicin to a patient via a local route of administration and thereby avoid undesirable side effects of systemic administration.

More particularly, senility- and noise-induced loss of hearing can be treated according to the present invention. It is known that there is an apoptosis of hair cells within the cochlear ear channels associated with some of these conditions. According to the present invention, this condition may be treated by administering drugs directly to the inner ear in order to minimize or delay this senility- or noise-induced hearing loss. Typical pharmaceutical compounds that may be useful include the calcium channel blocking agents, cyclosporins, as well as steroids.

Devices and methods in accordance with the present invention can also advantageously be used in the treatment of Meniere's disease. Particular medications which may be used in treating this disease are mentioned above and include, but not limited to, vasodilators, diuretics and steroids.

Devices and methods in accordance with the present invention can also advantageously allow for the gradual diffusion of medication across a membrane or into, e.g., the endolymphatic sac. By way of example and not of limitation, a hole is drilled into the endolymphatic sac or directly into the bone, and an implantable drug delivery device is secured into the resulting hole. The device may be screw-shaped or otherwise shaped so as to be self-anchoring, or it may be attached by sutures, screws, staples, or other methods known in the art. At the tip of the screw may be a permeable polymer that modulates delivery of the drug in a controlled manner. According to another embodiment of the present invention, the implantable drug delivery device can be implanted in the oval window or round window, and the drug from the device can leach into the inner ear to treat the condition for which the drug is selected.

In the methods of preventing or reducing ototoxicity of the present invention, various parameters associated with the patient's hearing and vestibular systems can be tested by methods well known in the art to establish pretreatment baseline values. After administration of the methionine protective agent, and over the course of chemotherapy and afterwards, ototoxic effects can be monitored by conventional tests, and the results can be compared to those obtained prior to treatment to determine if any change has occurred. If any impairment is observed, the amount and/or time of administration of the protective agent administered in conjunction with subsequent doses of the platinum-containing chemotherapeutic agent, loop diuretic agent, aminoglycoside antibiotic, iron chelating agent, quinine, quinidine, or exposure to noise or radiation, can be adjusted so as to reduce or prevent further ototoxic changes without substantially diminishing the antineoplastic effectiveness of the platinum-containing chemotherapeutic agent or radiation, the diuretic effect of the loop diuretic agent, etc. Similar modification of treatment parameters in the case of weight loss, gastrointestinal toxicity due to either the platinum-containing chemotherapeutic agent or radiation, neurotoxicity due to either the platinum-containing chemotherapeutic agent or radiation, alopecia due to either the platinum-containing chemotherapeutic agent or radiation, and overall patient condition/survival due to either the platinum-containing chemotherapeutic agent or radiation can be employed to optimize the protective effects of the protective agent with respect thereto. This can be achieved via appropriate testing and comparison of pre- and post-treatment values, e.g., patient weight and patient physical/medical/physiological condition, etc., with protocol adjustments being made as needed.

In various embodiments, the drug delivery device can be adapted for administration at, in or near the nasal cavity. In various embodiments, the drug delivery devices can be implanted at, in or near the nasal cavity. In various embodiments, the invention provides for a method for treating a mammal having or prone to a nasal disease condition, or treating a mammal prophylactically to prevent or reduce the occurrence or severity of a nasal disease condition, comprising providing a drug delivery device of the present invention, and administering a therapeutically effective amount of an agent capable of treating the eye disease condition via the drug delivery device. The method includes positioning a sustained released drug delivery system at an area wherein release of the agent is desired and allowing the agent to pass through the device to the desired area of treatment. Such devices provide sustained controlled release of various compositions to treat the nasal disease condition and lower the risk of detrimental local and systemic side effects. Accordingly, an embodiment of the invention is a method of treating a condition of the nose or nasal cavity of a mammal comprising the steps of accessing an internal anatomical site adjacent to the nasal cavity, and placing or implanting a drug delivery device in the internal anatomical site.

In various embodiments, the device can be adapted for administration at, in or near the prostate. In various embodiments, the devices can be implanted at, in or near the prostate. In various embodiments, the invention provides for a method for treating a mammal having or prone to a prostatic disease condition, or treating a mammal prophylactically to prevent or reduce the occurrence or severity of a prostatic disease condition, comprising providing a drug delivery device of the present invention, and administering a therapeutically effective amount of an agent capable of treating the prostatic disease condition via the drug delivery device. The method includes positioning a sustained released drug delivery system at an area wherein release of the agent is desired and allowing the agent to pass through the device to the desired area of treatment. Such devices provide sustained controlled release of various compositions to treat the prostatic disease condition and lower the risk of detrimental local and systemic side effects. Accordingly, an embodiment of the invention is a method of treating a condition of the prostate of a mammal comprising the steps of accessing an internal anatomical site adjacent to the prostate, and placing or implanting a drug delivery device in the internal anatomical site.

In various embodiments, the device can be adapted for administration at, in or near the bladder. In various embodiments, the devices can be implanted at, in or near the bladder. In various embodiments, the invention provides for a method for treating a mammal having or prone to a bladder disease condition, or treating a mammal prophylactically to prevent or reduce the occurrence or severity of a bladder disease condition, comprising providing a drug delivery device of the present invention, and administering a therapeutically effective amount of an agent capable of treating the bladder disease condition via the drug delivery device. In various embodiments, the bladder disease condition is incontinence. The method includes positioning a sustained released drug delivery system at an area wherein release of the agent is desired and allowing the agent to pass through the device to the desired area of treatment. Such devices provide sustained controlled release of various compositions to treat the bladder disease condition and lower the risk of detrimental local and systemic side effects. Accordingly an embodiment of the invention is a method of treating a condition of the bladder of a mammal comprising the steps of accessing an internal anatomical site adjacent to the bladder, and placing or implanting a drug delivery device in the internal anatomical site.

In various embodiments, the present invention provides for the surgical implantation of a drug delivery device, which includes larger scale cutting of the tissues of the patient in order to access the anatomical site in which the drug delivery device is to be implanted.

In various embodiments, the drug delivery device can be implanted subcutaneously to treat, to prevent, to reduce the occurrence or severity of the various disease conditions. In various embodiments, the device can maintain an effective concentration of the drug for at least 30 days, 60 days, 120 days, 150 days, 180 days, and at least one year.

Yet another particular embodiment of the present invention is a method for delivering, for an extended period of time, an effective amount of therapeutic agents to an affected site. Long term delivery of therapeutic agents is a particular embodiment of the present invention. Therefore, the present invention includes a drug delivery device that is placed within an anatomical site and is capable of delivering a therapeutic agent for at least a week. The duration of the drug delivery through the implanted drug delivery device to the effected site can be months to years. The delivery of these therapeutic agents can be linear in nature and the dosage is capable of remaining at therapeutic levels for weeks, months, or years.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Intravaginal Ring with Cellulose Polymer Hydrogel to Deliver Tenofovir

One example of the disclosed technology is an intravaginal ring containing a cellulose-based polymer hydrogel that releases the microbicide drug tenofovir (TFV). The ring platform for delivery of TFV is illustrated in FIG. 1. A core of ca. 15 mg drug is coated with a layer of semi-permeable polymer, polylactic acid (PLA) to form a drug pod. The drug pod is then incorporated into a pre-formed silicone IVR containing a cavity to hold the pod and a delivery window to expose a portion of the pod to the outside surface of the ring. The ring segment was molded in a single step using standard liquid silicone resin (LSR) injection molding techniques. The drug pod cavity extended through to the top of the ring. Prior to placement of the drug pod in the pod cavity in the silicone ring, a delivery window in the bottom of the cavity was punched with a 1 mm diameter biopsy punch. The hydrogel was applied to the pod and/or cavity as described below, and the drug pods were inserted and sealed in place with room temperature curing silicone.

Carboxymethylcellulose-Hydroxyethylcellulose Copolymer (CMC-HEC)

Figure 4:
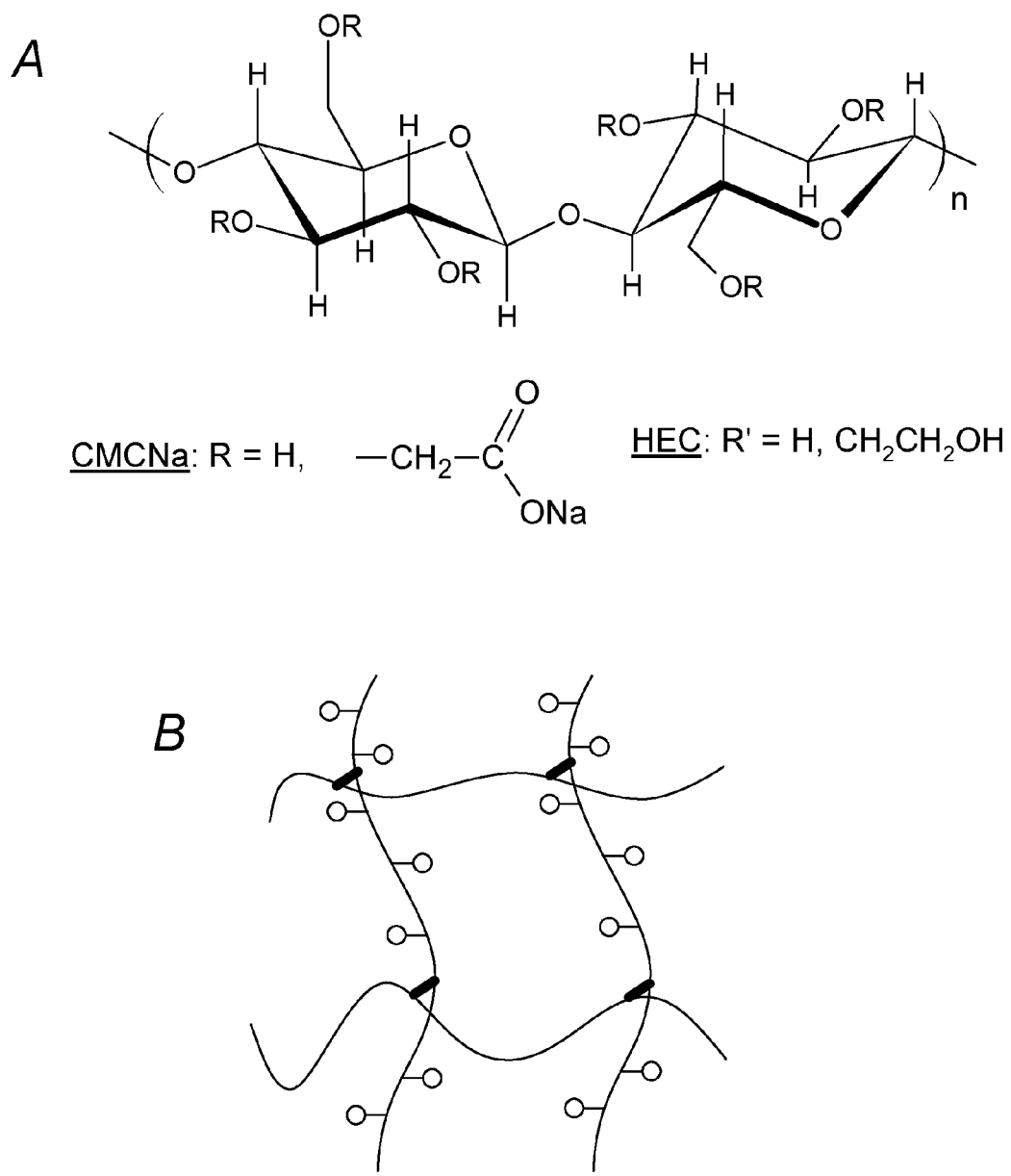
FIG. 4 depicts (a) Structures of CMCNa and HEC and (b) representation of CMCNa-HEC cross-linked polymer in accordance with various embodiments of the present invention. The DVS cross-linker is shown as thick lines, the CMCNa is shown by the thin lines with the circles representing the charged carboxylate sites, and the HEC is represented by the thin lines without attached circles.
Figure 5:
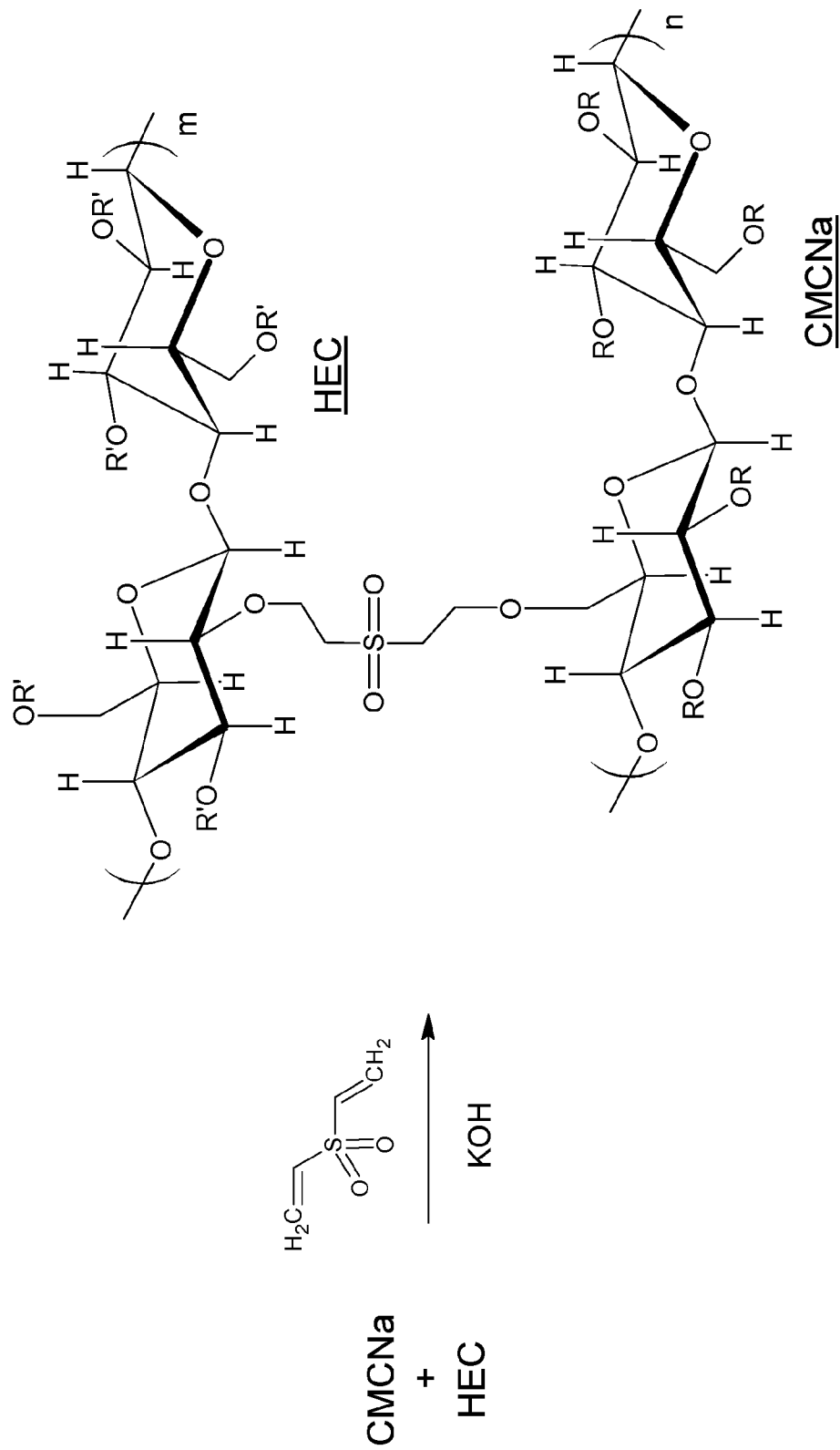
FIG. 5 depicts cross-linking reaction used in the preparation of CMCNa-HEC hydrogels in accordance with various embodiments of the present invention.

Copolymers of cellulose-based materials have been reported with applications in drug delivery and other applications requiring highly-swelled, hydrophillic gels.[2-11] A copolymer of carboxymethylcellulose sodium (CMCNa) and hydroxyethylcellulose (HEC) as shown in FIG. 4 was prepared by crosslinking CMCNa and HEC with a divinylsulfone crosslinking agent as shown in FIG. 5. This reaction, along with a number of related polymer preparations have been reported in the literature,[2,5,11] but these hydrogels have not previously been incorporated into intravaginal rings or used as wicks for drug delivery through a delivery window as disclosed here.

Hydrogel Preparation.

The CMC-HEC copolymer was prepared by cross-linking CMCNa (Fluka, Visc.=400-1000 mPa·s) and HEC (Aldrich, $M_w$=250 kDa) with divinylsulfone (DVS).[2,4] In a typical preparation, 125 μL DVS (Aldrich) was dissolved in 25 mL deionized $H_2O$ (d$H_2O$). To the DVS solution was added 0.375 g CMCNa and 0.125 g HEC (3:1 ratio) to give a ~2% w/v polymer solution. The polymer solution was stirred overnight to ensure complete dissolution, then 1 mL 0.5M KOH in d$H_2O$ was added to initiate the cross-linking reaction. Gel formation occurs within 24 hours. Gels for FTIR analysis were cast into thin films immediately after KOH addition by spreading a thin layer on a Teflon sheet and drying in air. For incorporation into IVRs, two methods were used: gel drying and in situ gel formation.

Hydrogel Drying.

Dry CMC-HEC granules were obtained by allowing the gel to form in a 50 mL beaker over 24 h. Excess cross-linker and other unreacted material was removed by successive replacements of the water in the beaker—typically 3 replacements of 5× the weight of the gel were used over a 48 h period. Gels were dried when necessary by removing the water from the beaker and replacing with acetone. The acetone was successively replaced with a fresh volume (2× hydrogel weight) to ensure removal of all of the water. The acetone was evaporated in air and the resulting polymer material dried at 40° C. and ground into a coarse powder.

In Situ Gel Formation.

Hydrogels were formed directly in the IVR drug pod cavity as shown in FIG. 6. A 75-100 μL aliquot of the gel solution just after addition of KOH was added to the empty drug pod cavity and allowed to fill both the delivery window and the bottom of the pod cavity. The pod cavity and delivery window were sealed with a Parafilm wrap. Following 24 h curing, the Parafilm was removed and the gel washed with d$H_2O$ to remove excess DVS and KOH. The drug pod was then placed in the cavity on top of the hydrogel, and the cavity sealed with room-temperature cure silicone (Nusil MED1-4213).

CMC-HEC Copolymer Characterization.

Figure 7:
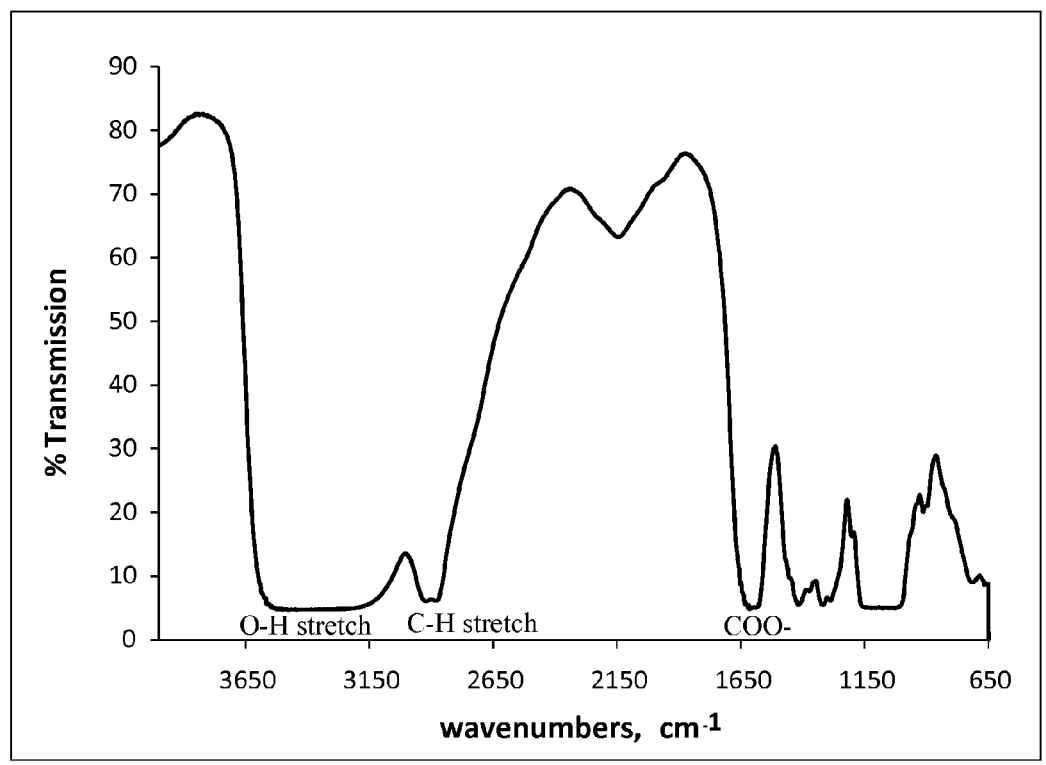
FIG. 7 depicts FTIR Spectrum of cast film of CMC-HEC copolymer in accordance with various embodiments of the present invention. The peak at 1600 $cm^{-1}$ is ascribed to unprotonated COO— groups on the CMC backbone.

For the carboxymethylcellulose-hydroxyethylcellulose copolymer, cross-linking as above leads to a viscous gel solution that can be cast as a thin film on a Teflon surface or dried and ground into a granular, soft powder. The FTIR spectrum of a cast film of a dessicated (dried) CMC-HEC hydrogel is shown in FIG. 7. The film was prepared by spreading a drop of CMC-HEC polymer solution on a Teflon sheet soon after the addition of KOH to initiate cross-linking. The film was covered, allowed to cure 24 h, then uncovered and allowed to dry. The dried film, resembling a piece of Saran Wrap film, was peeled from the Teflon surface and the FTIR spectrum obtained directly by transmission through the film. Further characterization of the films by NMR spectroscopy was attempted, but not possible as the hydrogels do not dissolve in appropriate deuterated solvents ($D_2O$, $CD_3OD$, DMSO-d6, and $CD_3CN$).

In Vitro Release of TFV from IVRs Containing CMCNa-HEC Hydrogel

Figure 8:
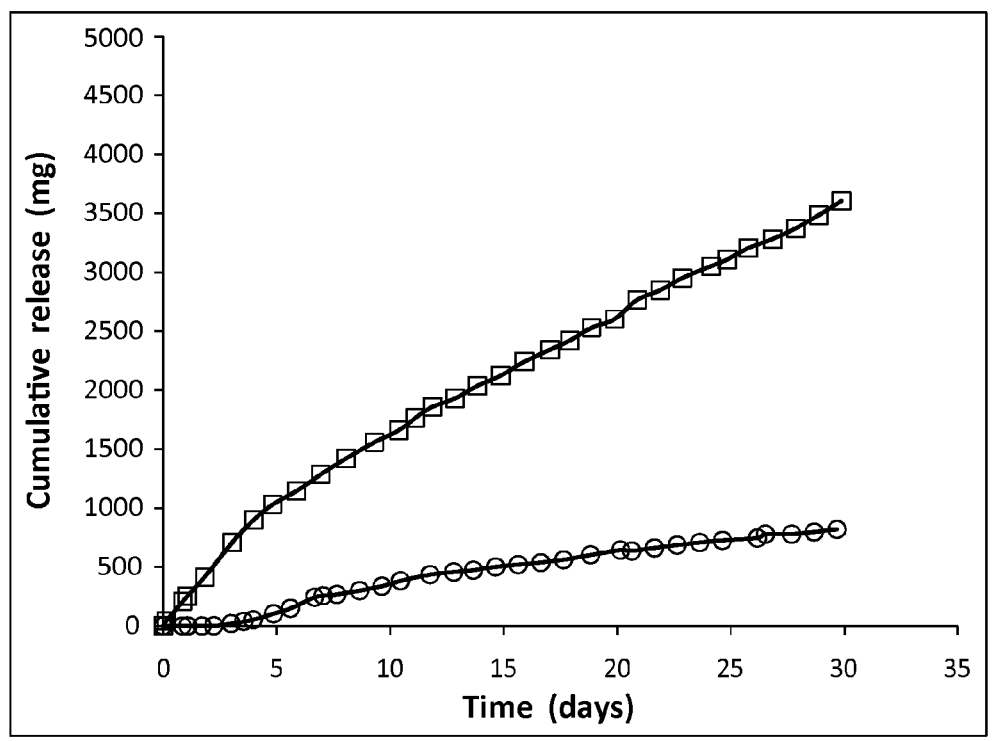
FIG. 8 depicts the average cumulative release for IVRs with no hydrogel (circles, 24 µg/day, n=4) and CMC-HEC hydrogel (squares, 100 µg/day, n=3) in accordance with various embodiments of the present invention.

The release of TFV from the hydrogel-containing IVR segments into VFS was compared to release from identical IVR segments with no hydrogel. FIG. 8 shows cumulative release of TFV as a function of time in CMC-HEC containing IVRs compared to IVRs with no hydrogel. The hydrogel acts as a wick filling the delivery window, drawing water into the drug pod and removing the lag time for release. The hydrogels perform a number of roles in the IVR, including: decreasing the variability in release rate from IVR-to-IVR, changing (i.e., either increasing or decreasing, depending on the material, implant design, and API) the release rate of TFV from the ring, eliminating the initial lag in TFV release observed in the original ring design, and filling the delivery window and preventing accumulation of matter within the window that may potentially impact the desired release rate. The inventors anticipated that the hydrogel would decrease the variability of release rate from IVR to IVR, but, there was also an unexpected, dramatic increase in the release rate (24 μg day$^{-1}$ without hydrogel and 100 μg day$^{-1}$ with hydrogel) and an elimination of the lag time to start of release in the hydrogel IVRs compared to those without hydrogel. These properties of the CMCNa-HEC hydrogel IVRs are important because they (a) provide a novel mechanism for increasing drug release, and (b) eliminate the delay in reaching a therapeutic drug level from the time of insertion of the IVR. The ability to release a therapeutically active amount of drug is problematic in typical matrix IVR designs where the drug must diffuse through the silicone matrix to be released. IVRs with the design of the present invention allow precise control of the drug release rate by multiple parameters: the hydrogel composition and physical properties (viscosity, extent of crosslinking), the number of drug pods, and the size of the delivery windows. The lag period in release start typically exhibited by non-hydrogel containing IVRs is likely due to variability in the wetting of the delivery window when it is initially air-filled.

Example 2

Intravaginal Ring with Polyvinylalcohol-Acrylate (PVA-MA) Co-Polymer Hydrogel to Deliver Tenofovir A second example of the disclosed technology is an intravaginal ring containing a polyvinylalcohol-acrylate (PVA-MA) polymer hydrogel that releases the microbicide drug tenofovir. The ring platform for the PVA-MA hydrogel IVR is identical to that described above for CMCNa-HEC, with PVA-MA in place of the CMCNa-HEC polymer.
Polyvinylalcohol-Acrylate (PVA-MA) Polymer Hydrogel Preparation and Characterizaton.
PVA-MA Macromer Synthesis Polyvinyl alcohol was modified with acrylate groups by esterification of PVA hydroxyl groups with glycidyl methacrylate (GMA) using a modification of the method of Martens, et al.[12] The degree of substitution (D.S.) is the ratio of acrylate groups to total number of hydroxyl groups on the PVA backbone, and is controlled by the relative ratios of GMA and PVA used in the reaction. Macromers were prepared with two different PVA molecular weights, 18 and 63.5 kDa. In a typical preparation, 1 g PVA (Sigma) was dissolved in 25 mL dimethylsulfoxide (DMSO). Gentle heating was required. To the PVA solution was added 0.5 g dimethylaminopyridine (DMAP). The solution was sparged with argon (Ar) to remove $O_2$, and the reaction maintained under an Ar atmosphere. Glycidyl methacrylate was added stoichiometrically based on the desired D.S., and the solution stirred 48 h in the dark, protecting the reaction from light by wrapping the flask in Al foil. After 48 h, the DMAP was neutralized with 980 µL conc. HCl to prevent alkaline hydrolysis of the methacrylate ester.

Figure 9:
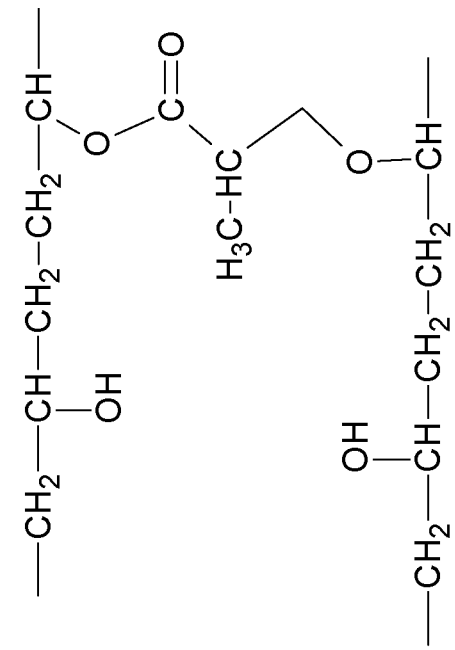
FIG. 9 depicts photochemical cross-linking of PVA-MA macromer chains in accordance with various embodiments of the present invention.
Figure 9:
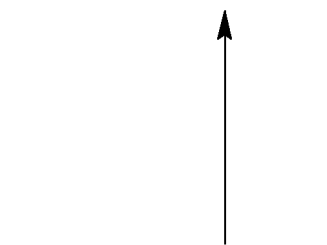
Figure 9:
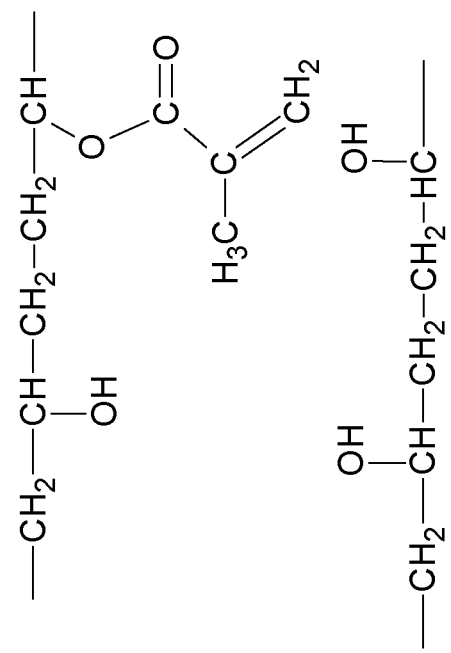
Figure 10:
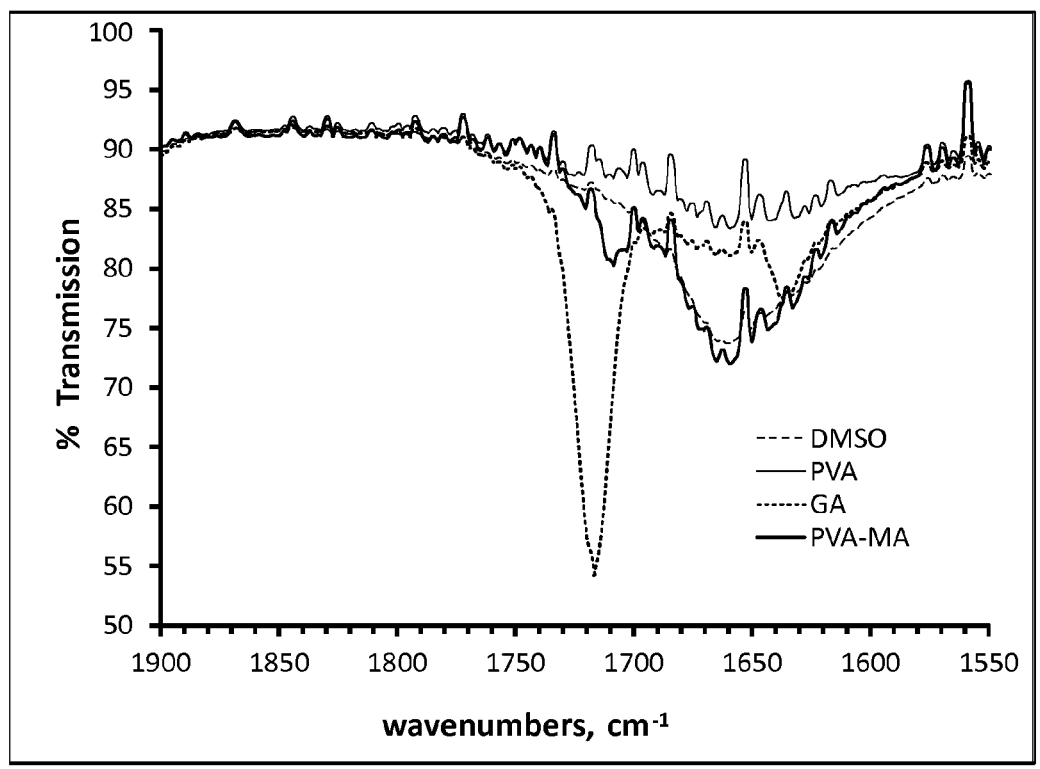
FIG. 10 depicts FTIR spectra of PVA, GA, and PVA-MA in DMSO solution showing C=O stretch at 1715 $cm^{-1}$ and C=C stretch at 1630 $cm^{-1}$ in GA and absence of a C=O stretch in PVA in accordance with various embodiments of the present invention. Upon macromer formation, the C=O stretch is observed at 1710 $cm^{-1}$ in PVA-MA, indicating substitution of acrylate on the PVA backbone. The C=C stretch in the PVA-MA sample is obscured by absorption from DMSO.

The macromer was purified by dialysis against $dH_2O$ to remove unreacted GMA and DMAP. Dialysis was carried out in dialysis tubing with a 12,000 g/mol molecular weight cut-off for 2 days, changing the $dH_2O$ twice daily. For D.S.≤5% acrylate, the macromer is water soluble. For D.S.>5%, the macromer precipitates as a white waxy solid. The value of D.S. was determined by nuclear magnetic resonance (NMR) spectroscopy. Macromer samples were dissolved in DMSO-d6, and $^1$H-NMR spectra were acquired with a Varian Mercury 300 MHz instrument. The value of D.S. is calculated as the ratio of the integration of the vinyl proton peaks (average of integration values of peaks at 5.50 and 6.20 ppm) to that of the unsubstituted methine moiety at 4.07-4.20 ppm, expressed as a percentage.
Cross-Linking of PVA-MA Macromer Cross-linking was carried out on a ~9% w/v solution of macromer in DMSO (D.S.>5%) or $H_2O$ (D.S.≤5%). The photoinitiator 2-hydroxy-1-[4-(hydroxyethoxy)phenol]-2-methyl-1-propanone (Aldrich), was added at 0.05% w/v. The macromer solution was then placed in the drug cavity/delivery window of an IVR using a micropipette as described above for CMCNa-HEC, or pipetted onto a glass plate to form a thin film disk. Photochemical cross-linking was carried out by irradiating the macromer sample using a Xe lamp UV-gun (λ=355 nm) for 1-15 min. The macromer solution (un-cross-linked) could also be placed in the delivery window of an IVR after manufacture and cross-linked photochemically with the drug pod in place. The cross-linking reaction is shown in FIG. 9.
PVA-MA Co-Polymer Characterization Prior to crosslinking, PVA-MA macromer solutions in DMSO can be cast into thin films or loaded dropwise into the delivery window and drug pod cavities of IVRs. The solution viscosity is controlled by concentration of PVA-MA in solution, and can be varied from an easily flowing solution, to a thick, syrup-like consistency. Three PVA-MA macromers were prepared by varying either the amount of GMA relative to PVA (5% or 10%) or the PVA average molecular weight (18 or 63.5 kDa). FTIR spectra of PVA, GMA, and PVA-MA macromer are shown in FIG. 10. These spectra clearly show the macromer formation as the PVA spectrum does not contain a C═O stretching band in the 1700 cm-1 region, but the PVA-MA macromer shows a band at 1710 cm$^{-1}$ indicating replacement of hydroxyl groups with the acrylate functionality.

Figure 11:
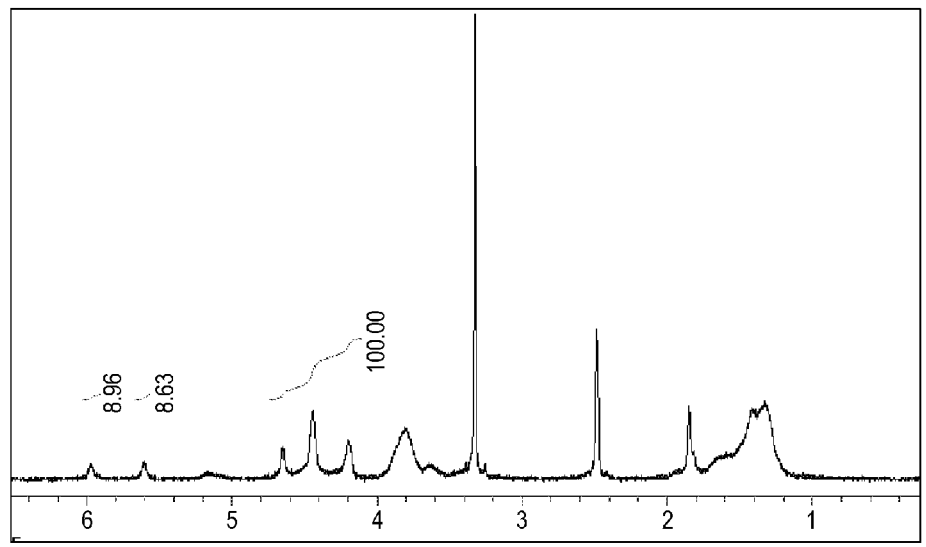
FIG. 11 depicts $^1$H-NMR spectra of PVA-MA macromers in DMSO-d6 in accordance with various embodiments of the present invention. (A) 63.5 kDa PVA; acrylation: 10% (theoretical), 8.8% (calculated) (B) 18 kDa PVA; acrylation: 10% (theoretical), 12.5% (calculated) (C) 63.5 kDa PVA; acrylation: 5% (theoretical), 5.1% (calculated).
Figure 11:
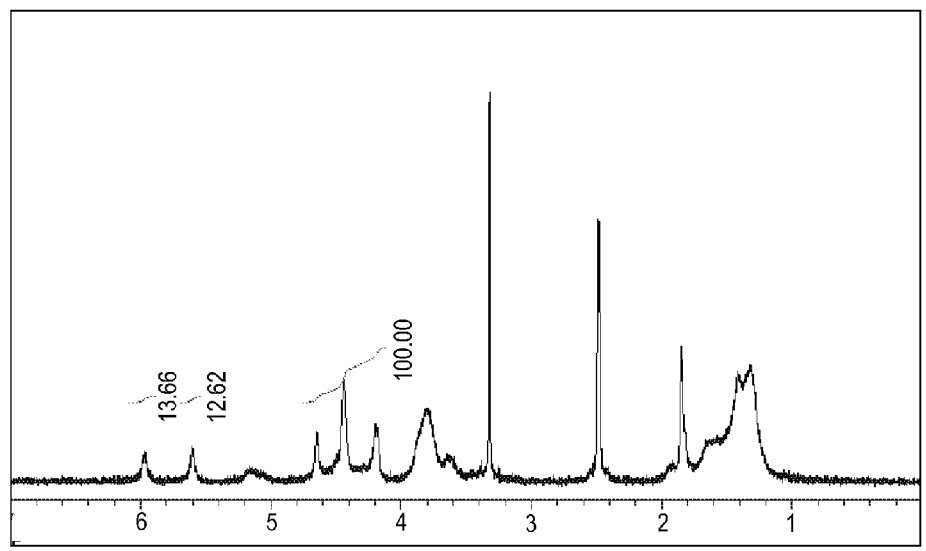
Figure 11:
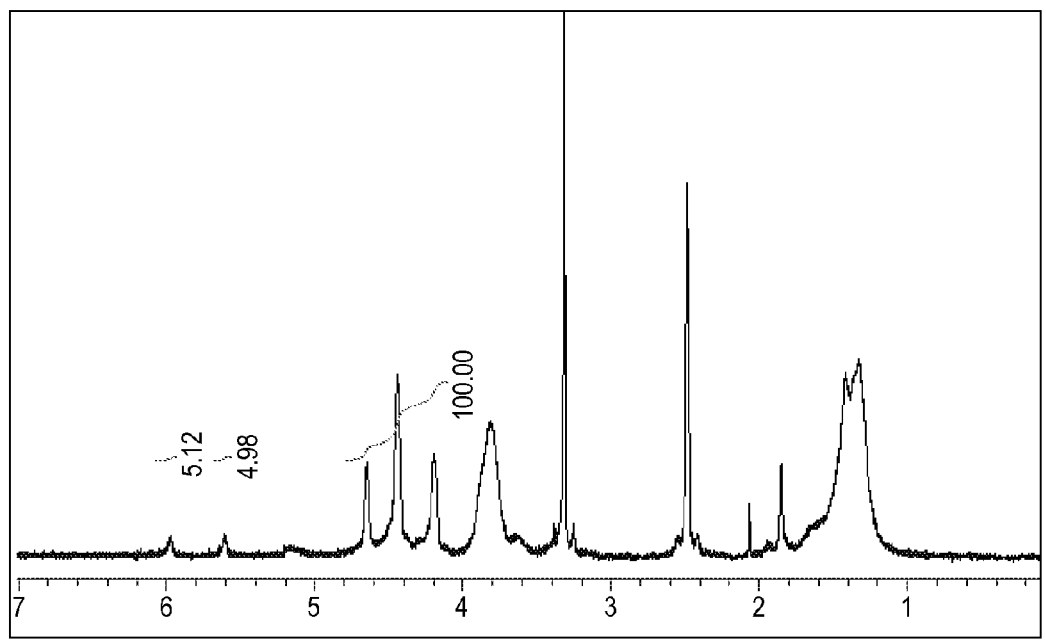
Figure 12:
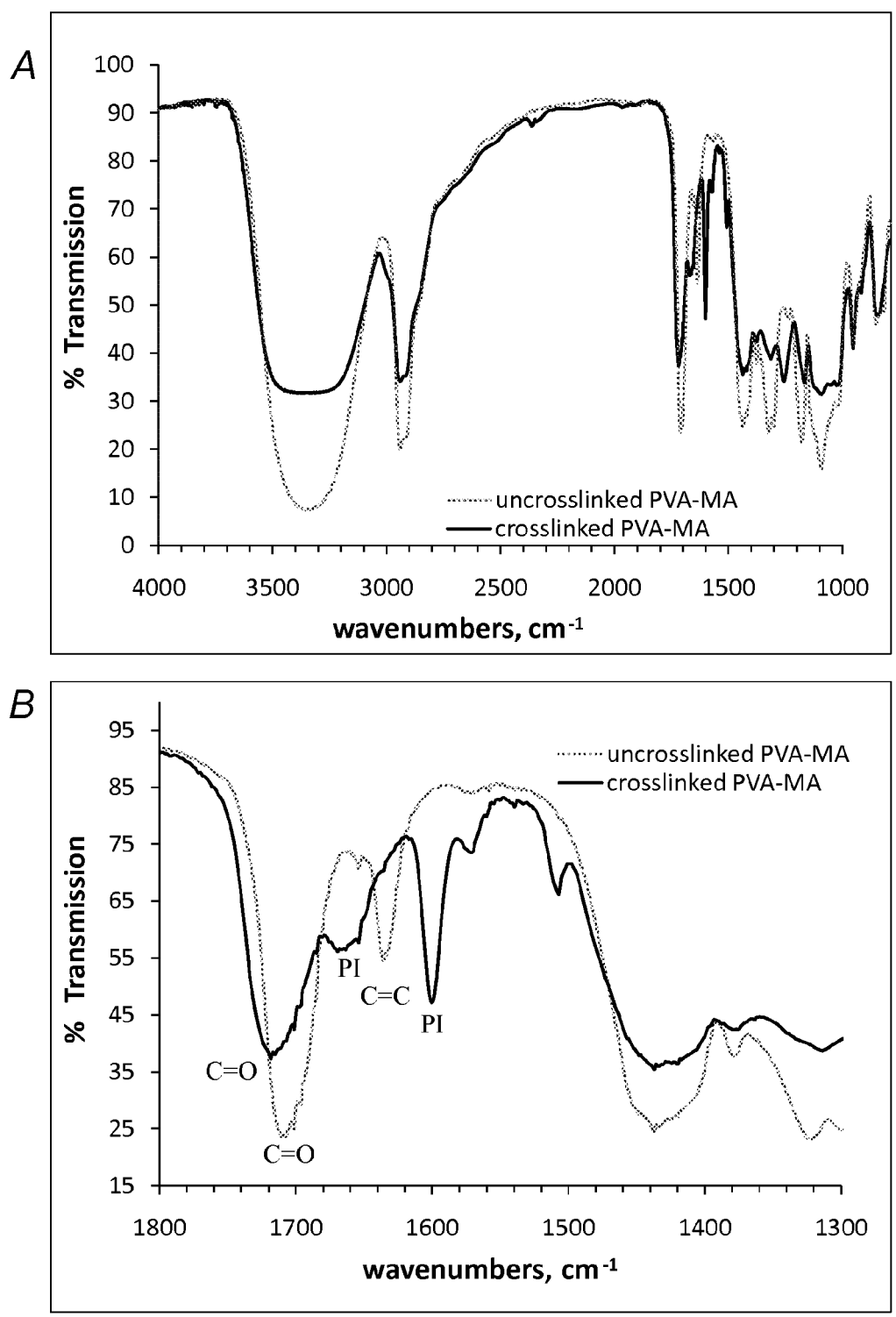
FIG. 12 depicts FTIR spectra of cast films of PVA-MA before and after cross-linking, (a) full spectrum, (b) C=O and C=C stretching region. (PI=photoinitiator) in accordance with various embodiments of the present invention.

The degree of acrylate substitution in the PVA backbone was determined by NMR spectroscopy as described above. The percent substitution is given by the ratio of the average integration of the two acrylate protons at $\delta_H$ 5-6 ppm to the integration of the PVA backbone protons at $\delta_H$ 4-5 ppm. $^1$H-NMR spectra of the three macromers are shown in FIG. 11, along with the theoretical and measured acrylate substitution percentages.
PVA-MA Co-Polymer Cross-Linking The cross-linking of PVA-MA macromers was investigated using FTIR spectroscopy. FIG. 12 shows FTIR spectra of a PVA-MA cast film before and after 15 min. UV-cross-linking. The spectra were acquired by transmission through the film with no solvent; thus, the C═C stretching bands that were obscured by DMSO absorption in the macromer solution spectra are visible in the films. The carboxyl stretch from the acrylate moiety at 1708 cm$^{-1}$ shifts to 1718 cm$^{-1}$ upon cross-linking due to loss of conjugation with the C═C bond. The cross-linking reaction is shown in Scheme VI. The C═C stretch at 1635 cm$^{-1}$ disappears upon cross-linking at the acrylate vinyl moiety. The bands at 1600 cm$^{-1}$ (aromatic ring C—C stretch) and 1660 cm$^{-1}$ (C═O stretch) are from the photoinitiator (PI), which was not present in the uncross-linked film.

Figure 13:
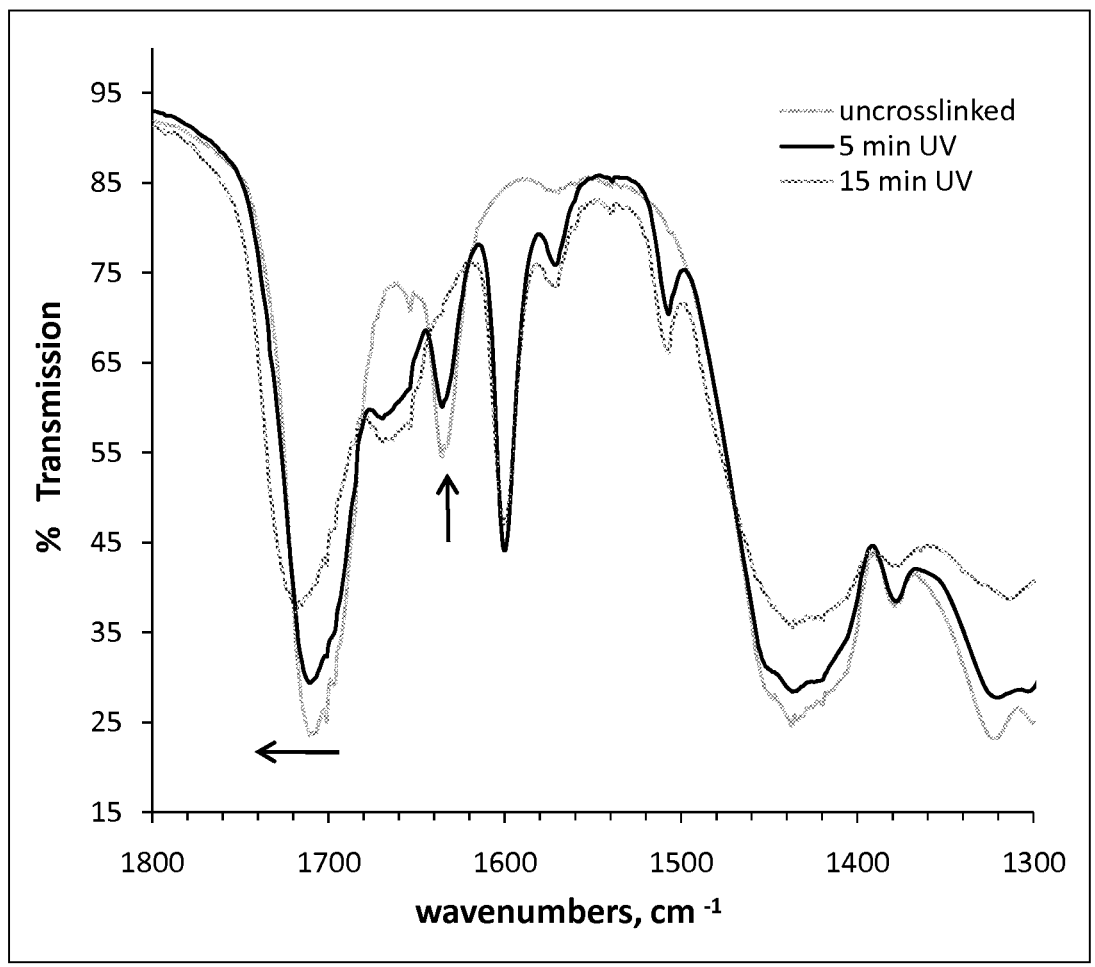
FIG. 13 depicts FTIR spectrum of PVA-MA film cross-linked by irradiating for 0, 5, and 15 minutes in accordance with various embodiments of the present invention. The C=O stretch at 1708 $cm^{-1}$ in the un-cross-linked film gradually shifts to higher energy as conjugation with the acrylate C=C double bond is lost. The C=C stretch at 1630 $cm^{-1}$ from the acrylate moiety disappears as the acrylate forms a saturated ether bond with a —OH from another PVA-MA chain.
Figure 14:
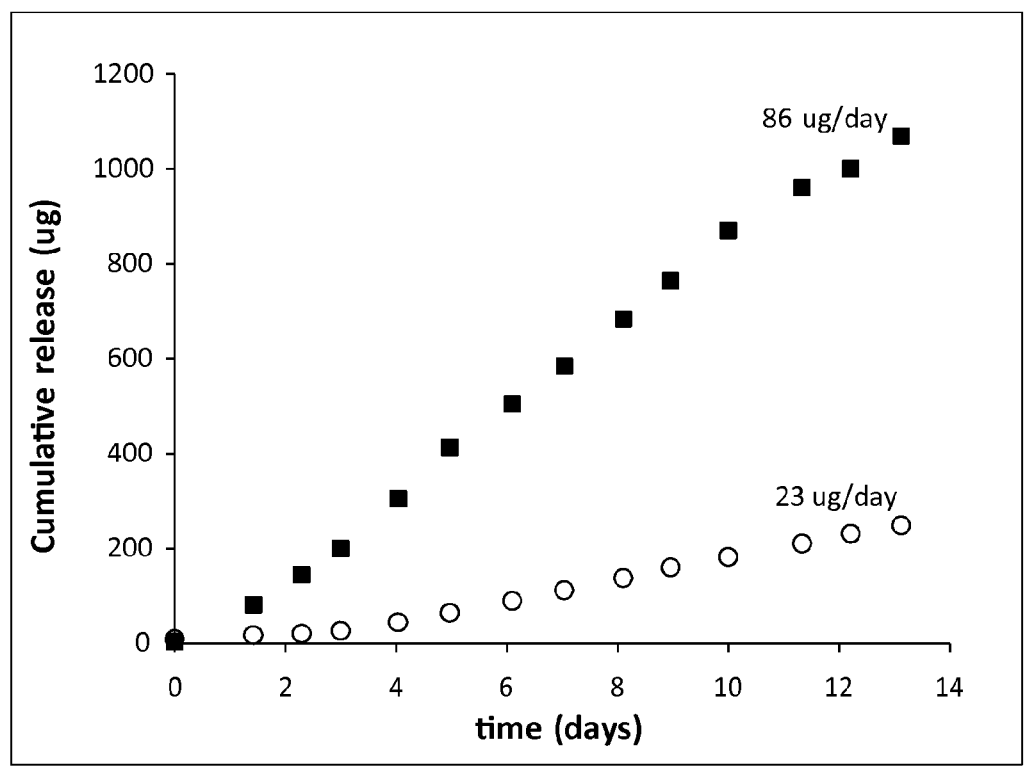
FIG. 14 depicts the average cumulative release for IVRs with un-cross-linked PVA-MA macromer (open circles, n=3) and cross-linked PVA-MA hydrogel (closed circles, n=3) in accordance with various embodiments of the present invention.

Changes in the FTIR spectrum of a PVA-MA macromer as a function of irradiation time are shown in FIG. 13. Here, the C═C stretching band decreases with increasing irradiation time as the vinyl group reacts with —OH on another PVA chain to form an ether cross-link. The C═O stretch from the acrylate shifts to higher energy as the conjugation with the C═C bond of the acrylate vinyl moiety is lost.
In Vitro Release of Tenofovir from PVA-MA Hydrogel IVRs FIG. 14 shows the average cumulative release for a set of IVRs containing PVA-MA hydrogel. Three IVRs contained PVA-MA co-polymer with no cross-linking and three had PVA-MA that had been cross-linked in situ in the delivery window using 15 minutes photolysis with UV light. The PVA-MA hydrogels do not release TFV as rapidly as do otherwise identical IVRs with the CMC-HEC hydrogel. Carboxymethylcellulose is a superabsorbant material and it is expected that it would be much more wetted in aqueous solution than PVA, potentially providing a better "wicking" matrix for rapid TFV transport through the delivery window. For the PVA-MA IVRs, an initial lag in the release rate is observed the un-cross-linked samples, but is significantly reduced in the cross-linked samples. The PVA-MA hydrogels, however, allow the extent of cross-linking to be controlled, and allow much more precise control of drug release rate by modifying the hydrogel than do the CMCNa-HEC hydrogels. In the PVA-MA system, the extent of cross-linking can be determined by the degree of methacrylate substitution (% MA per total polymer mass) in the PVA polymer, the size of the PVA polymer starting material (which, along with D.S., determines total number of cross-link sites per PVA chain), and the length of time the PVA-MA macromere is UV irradiated (determines the fraction of available cross-link sites that are actually cross-linked).

Comparison of Examples 1 and 2

Figure 15:
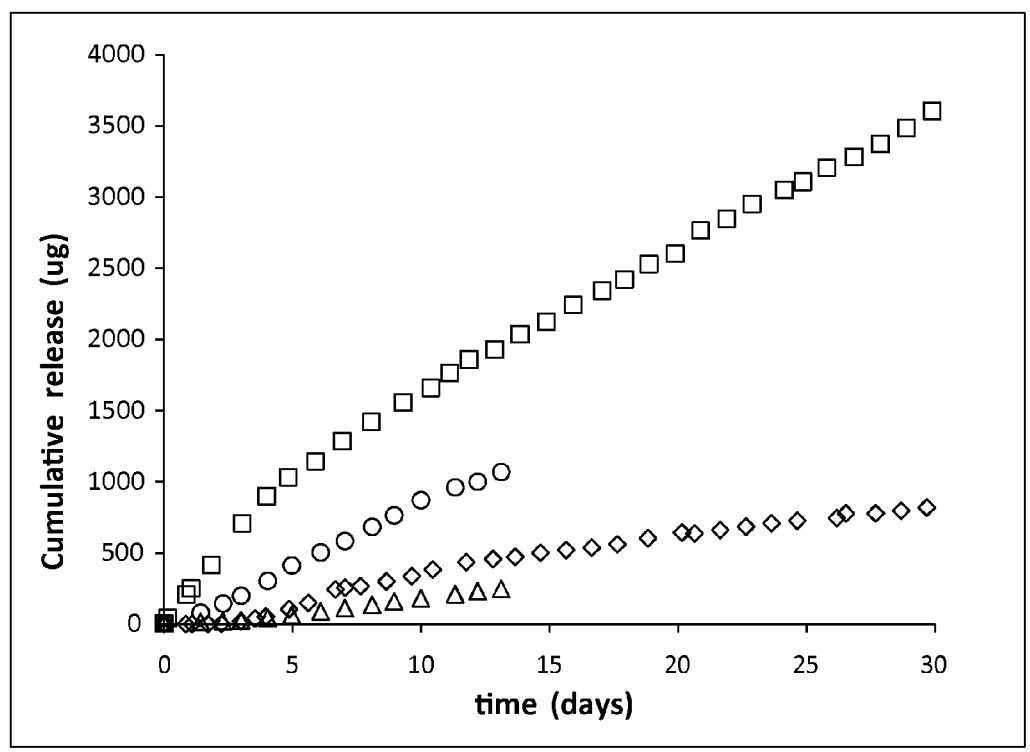
FIG. 15 depicts the average cumulative release for IVRs with no hydrogel (diamonds), CMC-HEC hydrogel (squares), un-cross-linked PVA-MA (triangles) and cross-linked PVA-MA (circles) in accordance with various embodiments of the present invention.

FIG. 15 shows the average cumulative release of TFV for all three hydrogel IVRs and a non-hydrogel IVR plotted together. The un-crosslinked PVA-MA IVR releases at nearly the same rate as the IVR with no hydrogel. This indicates that potentially the PVA-MA macromere dissolves and is removed from the delivery window quickly, resulting essentially in a non-hydrogel IVR. Cross-linking the PVA-MA doubles the release rate compared to the non-cross-linked PVA-MA IVR, and the CMC-HEC hydrogel IVR releases at double the rate of the cross-linked PVA-MA IVR.

REFERENCES

1. Vladkova, T. "Surface modification of silicone rubber with poly(ethylene glycol) hydrogel coatings." *J. Applied Polymer Science*, 2004, 92, 1486.
2. Anbergen, U.; Oppermann, W. "Elasticity and Swelling Behavior of Chemically Cross-linked Cellulose Ethers in Aqueous Systems." *Polymer* 1990, 31, 1854.
3. Baar, A.; Kulicke, W. M.; Szablikowski, K.; Kiesewetter, R. "Nuclear-Magnetic-Resonance Spectroscopic Characterization of Carboxymethylcellulose." *Macromolec. Chem. Phys.* 1994, 195, 1483.
4. Esposito, F.; DelNobile, M. A.; Mensitier, G.; Nicolais, L. "Water sorption in cellulose-based hydrogels." *J. Appl. Polym. Sci.* 1996, 60, 2403.
5. Lenzi, F.; Sannino, A.; Borriello, A.; Porro, F.; Capitani, D.; Mensitieri, G. "Probing the degree of crosslinking of a cellulose based superabsorbing hydrogel through traditional and NMR techniques." *Polymer* 2003, 44, 1577.
6. Barbucci, R.; Magnani, A.; Consumi, M. "Swelling behavior of carboxymethylcellulose hydrogels in relation to cross-linking, pH, and charge density." *Macromolecules* 2000, 33, 7475.
7. Capitani, D.; Mensitieri, G.; Porro, F.; Proietti, N.; Segre, A. L. "NMR and calorimetric investigation of water in a superabsorbing crosslinked network based on cellulose derivatives." *Polymer* 2003, 44, 6589.
8. Chambin, O.; Champion, D.; Debray, C.; Rochat-Gonthier, M. H.; Meste, M. L.; Pourcelot, Y. "Effects of different cellulose derivatives on drug release mechanism studied at a preformulation stage." *Journal of Controlled Release* 2004, 95, 101.
9. Lionetto, F.; Sannino, A.; Maffezzoli, A. "Ultrasonic monitoring of the network formation in superabsorbent cellulose based hydrogels." *Polymer* 2005, 46, 1796.
10. Lionetto, F.; Sannino, A.; Mensitieri, G.; Maffezzoli, A. "Evaluation of the degree of crosslinking of cellulose-based superabsorbent hydrogels: A comparison between different techniques." *Macromol. Symp.* 2003, 200, 199.
11. Sannino, A.; Nicolais, L. "Concurrent effect of microporosity and chemical structure on the equilibrium sorption properties of cellulose-based hydrogels." *Polymer* 2005, 46, 4676.
12. Martens, P.; Anseth, K. S. "Characterization of hydrogels formed from acrylate modified poly(vinyl alcohol) macromers." *Polymer* 2000, 41, 7715.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader embodiments and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A drug delivery device, comprising:
    at least one core comprising a first active pharmaceutical ingredient ("API");
    a first coating layer that is permeable and/or semi-permeable to the API covering at least a portion of the at least one core;
    a second coating layer that is impermeable to the API, covering at least a portion of the first coating layer; and
    a delivery window to provide passage of the API through the second coating layer,
    wherein the API diffuses toward the exterior of the device.
2. The drug delivery device of claim 1, comprising at least two cores, wherein a first core of the at least two core comprises the first API, and a second core of the at least two cores comprises a second API.

3. The drug delivery device of claim 1, wherein the at least one core comprises a second API.

4. The drug delivery device of claim 1, further comprising a wicking material to modify the rate of transport of the API through the delivery window.

5. The drug delivery device of claim 4, wherein delivery window is completely filled by the wicking material.

6. The drug delivery device of claim 4, wherein the delivery window is partially filled by the wicking material.

7. The drug delivery device of claim 4, wherein the wicking material is positioned through the delivery window passage.

8. The drug delivery device of claim 4, wherein the wicking material coats one or more inside walls of the delivery window.

9. The drug delivery device of claim 4, wherein the wicking material is chemically bound to at least a portion of the second coating layer.

10. The drug delivery device of claim 1, further comprising a third coating layer between the first coating layer and the second coating layer, the third coating layer covering at least a portion of the first coating layer to slow the release of the API.

11. The drug delivery device of claim 1, wherein the first coating layer comprises polylactic acid polymer, polyvinyl alcohol, or combinations thereof.

12. The drug delivery device of claim 1, wherein the second coating layer is selected from the group consisting of silicone, polyethylene ("PE"), ethylene vinyl acetate ("EVA") and combinations thereof.

13. The drug delivery device of claim 4, wherein the wicking material comprises a hydrophilic polymer or a fiber material.

14. The drug delivery device of claim 13, wherein the wicking material comprises carboxymethylcellulose-hydroxyethylcellulose ("CMCHEC") copolymer.

15. The drug delivery device of claim 13, wherein the wicking material comprises polyvinylalcohol-acrylate ("PVA-MA") copolymer.

16. The drug delivery device of claim 13, wherein the wicking material comprises polyethylene glycol-methacrylate copolymer.

17. The drug delivery device of claim 13, wherein the fiber material is selected from the group consisting of silk, cotton, Nafion and combinations thereof.

18. The drug delivery device of claim 4, configured as an intravaginal ring, a diaphragm, a pessary, a suppository, or a punctual plug.

19. The drug delivery device of claim 1, configured as an intravaginal ring wherein the API comprises tenofovir.

20. A method, comprising:
providing a drug delivery device of claim 1; and
administering the drug delivery device into a subject in need thereof to deliver the active pharmaceutical ingredient.

21. The method of claim 20, wherein a disease condition is treated or reduced.

22. The method of claim 21, wherein disease condition is a human immunodeficiency virus (HIV) infection.

23. The method of claim 20, wherein the active pharmaceutical ingredient is selected from the group consisting of atazanavir, didanosine, efavirenz, emtricitabine, lamivudine, lopinavir, nevirapine, raltegravir, ritonavir, saquinavir, stavudine, tenofovir, tenofovir disoproxil fumarate, zidovudine, acyclovir, famciclovir, valcyclovir, morphine, buprenorphine, estrogen, progestin, progesterone, cyclosporine, a calcineurin inhibitor, prostaglandin, a beta-blocker, gentamycin, corticosteroid, a fluoroquinolone, insulin, an antineoplastic drug, anti-nausea drug, a corticosteroid, an antibiotic, morphine buprenorphine, a VEGF inhibitor, and combinations thereof.

24. The method of claim 20, wherein the drug delivery device is adapted for a route of administration selected from the group consisting of: sub-dermal, sub-cutaneous, systemic, local, epidural, intra-lesional, intra-tumor, intra-punctal and combinations thereof.

25. The method of claim 20, wherein the disease condition is selected from the group consisting of hyperhomocysteinemia, chronic renal failure, end stage renal disease, hemodialysis, peritoneal dialysis, vascular dementia, cardiovascular disease, stroke, cerebrovascular accidents, thrombotic disorder, hypercoagulable states, venous thrombosis, deep vein thrombosis, thrombophlebitis, thromboembolic disease, ischemic stroke, restenosis after percutaneous transluminal coronary angioplasty (PTCA), preeclampsia, vasculitis, digital ischemia, multifocal osteonecrosis, retinal vein occlusion, glaucoma, miscarriage, pregnancy complication, placental abruption, transplantation, diabetic retinopathy, ischemic bowel disease, cerebral vein thrombosis, atherosclerosis, coronary artery disease, penile venous thrombosis, impotence, central venous thrombosis, peripheral artery disease, intermittent claudication, hemorrhagic colitis, radiation enteritis, radiation colitis, visceral ischemia, acute mesenteric ischemia, chronic mesenteric ischemia, hypertension, microangiopathy, macroangiopathy, recurrent leg ulcer, carotid stenosis, occlusive vascular disease, arterial aneurysm, abdominal aortic aneurysm, congestive heart failure, hepatopulmonary syndrome, high flow state associated with chronic liver disease, migraine headache, vascular headache, dizziness, lightheadedness, orthostatic intolerance, postural hypotension, postural hypotension, postural orthostatic tachycardia syndrome, idiopathic pulmonary fibrosis, pulmonary hypertension, angioedema, vaso-vagal faints, neuroleptic malignant syndrome, learning disorder, learning disability, insomnia, dementia, age associated memory impairment, attention deficit/hyperactivity disorder (ADHD), mild cognitive impairment, Alzheimer's disease, Down's syndrome, autism, Parkinson's disease, depression, anxiety or anxiety disorder, Asperger syndrome, glucose intolerance, diabetes, reactive hypoglycemia, metabolic syndrome, low cortisol, low cortisol, hypothalamus-pituitary-adrenal dysfunction, myasthenia gravis syndrome, osteoporosis, autoimmune polyendocrine syndrome, chronic fatigue syndrome (CFS), central sensitivity syndrome, angina, syndrome X, chronic neck pain syndrome, chronic neuromuscular pain, osteoarthritis, muscle tension headache, chronic headache, cluster headache, temporalis tendonitis, sinusitis, atypical facial pain, trigeminal neuralgia, facial and neck pain syndrome, temperomandibular joint syndrome, idiopathic chronic low back pain, endometriosis, painful abdominal adhesions, chronic abdominal pain syndrome, coccydynia, pelvic floor myalgia (levator am spasm), polymyositis, postherpetic neuralgia, polyradiculoneuropathies, mononeuritis multiplex, reflex sympathetic dystrophy, neuropathic pain, vulvar vestibulitis, vulvodynia, chronic regional pain syndrome, osteoarthritis, fibrositis, chronic visceral pain syndrome, female urethral syndrome, painful diverticular disease, functional dyspepsia, nonulcer dyspepsia, non-erosive esophageal reflux disease, acid-sensitive esophagus, interstitial cystitis, chronic pelvic pam syndrome, chronic urethral syndrome, chronic prostatitis, primary dysmenorrheal, dyspareunia, premenstrual syndrome (PMS), vulvodynia, ovarian remnant syndrome, ovulatory pain, pelvic congestion syndrome, myofasical pain syndrome, fibromyalgia polymyalgia rheumatica, Reiter's syndrome (reactive arthritis), rheumatoid arthritis, spondyloarthropathy, functional somatic syndromes, chronic regional pain syndromes, post-polio syndrome, functional somatic syndrome, rhinitis, asthma, multiple chemical sensitivity syndrome, reactive airway dysfunction syndrome, dysnomia, sick building syndrome, asthma, idiopathic pulmonary fibrosis, idiopathic pulmonary hypertension, dysphagia, gastroparesis, functional diarrhea, chronic constipation, defecation dysfunction, dysuria, atonic bladder, neurogenic bladder, irritable bowel syndrome (IBS), ileus, chronic idiopathic pseudoobstruction, Ogilvie's syndrome, restless leg syndrome, immune dysfunction syndrome, multiple sclerosis (MS), eczema, psoriasis, atopic dermatitis, dermatitis, Crohn's disease, ulcerative colitis, ulcerative proctitis, pouchitis, nonspecific ulcerative colitis, inflammatory bowel disease (IBD), celiac disease, diversion colitis, collagenous colitis, lymphocytic colitis, blind loop syndrome, nonalcoholic steatohepatitis (NASH), fatty liver, chronic liver disease, cirrhosis, spontaneous bacterial peritonitis, postoperative ileus, systemic lupus erythematosis, mixed connective tissue disorder, undifferentiated connective tissue disorder, Raynaud's phenomenon, Kawasaki syndrome, polymyositis, dermatomyositis, myositis, multiple autoimmune syndrome, Sjogren's syndrome, lichen planus, idiopathic uveitis, gingivitis, stomatitis, otitis, necrotizing enterocolitis, intensive care unit (ICU) multiple organ failure, primary biliary cirrhosis, idiopathic myelofibrosis, polyarteritis *nodosa*, eosinophilic pleural effusion, eosinophilic gastroenteritis, eosinophilic esophagitis, graft vs. host disease, Grave's disease, idiopathic thyroid failure, Hashimoto's thyroiditis, autoimmune hepatitis, pancreatitis, CREST syndrome, autoimmune cholangitis, ankylosing spondylitis, atopic dermatitis, vitiligo, scleroderma, autoimmune ear disease, polyangiitis overlap syndrome, primary sclerosing cholangitis, Gulf War syndrome, myalgic encephalomyelitis, food sensitivity, dysregulation spectrum syndrome, post-traumatic stress disorder (PTSD), benign tumor, malignant tumor, cancer and combinations thereof.

\* \* \* \* \*